US 12,357,677 B2
Kang et al.
Jul. 15, 2025

(54) VIRUS INFECTION USING PHARMACEUTICAL COMPOSITION COMPRISING IMMUNOGLOBULIN Fc-FUSED INTERLEUKIN-7 FUSION PROTEIN

(71) Applicant: GENEXINE, INC., Seongnam-si (KR)

(72) Inventors: Moon Cheol Kang, Pohang-si (KR); Young Woo Choi, Pohang-si (KR); Donghoon Choi, Yongin-si (KR); Young Chul Sung, Seoul (KR)

(73) Assignee: GENEXINE, INC., Seongnam-si (KR)

(*) Notice: Subject to any disclaimer, the term of this patent is extended or adjusted under 35 U.S.C. 154(b) by 386 days.

This patent is subject to a terminal disclaimer.

(21) Appl. No.: 17/838,382

(22) Filed: Jun. 13, 2022

(65) Prior Publication Data

US 2023/0015320 A1 Jan. 19, 2023

Related U.S. Application Data

(63) Continuation of application No. 15/777,437, filed as application No. PCT/KR2016/013966 on Nov. 30, 2016, now Pat. No. 11,357,827.

(60) Provisional application No. 62/263,262, filed on Dec. 4, 2015.

(51) Int. Cl.
A61K 38/20 (2006.01)
A61K 9/00 (2006.01)
A61K 47/68 (2017.01)
A61P 11/00 (2006.01)
A61P 31/16 (2006.01)

(52) U.S. Cl.
CPC ........ A61K 38/2046 (2013.01); A61K 9/0043 (2013.01); A61K 47/68 (2017.08); A61K 47/6813 (2017.08); A61P 31/16 (2018.01); A61P 11/00 (2018.01)

(58) Field of Classification Search
CPC ............. A61K 38/2046; A61K 47/68; A61K 47/6813; C07K 2319/00; C07K 14/5418; C07K 2319/30

See application file for complete search history.

(56) References Cited

U.S. PATENT DOCUMENTS

| 5,093,242 | A | 3/1992 | Bachmair et al. |
| 6,153,380 | A | 11/2000 | Nolan et al. |
| 7,585,947 | B2 | 9/2009 | Morre et al. |
| 7,589,179 | B2 | 9/2009 | Gillies et al. |
| 8,153,114 | B2 | 4/2012 | Morre et al. |
| 10,208,009 | B2 | 2/2019 | Yang et al. |
| 10,844,104 | B2 | 11/2020 | Yang et al. |
| 2002/0127564 | A1 | 9/2002 | Nolan |
| 2005/0054054 | A1* | 3/2005 | Foss ............... C07K 14/5418 435/325 |
| 2005/0164352 | A1* | 7/2005 | Lauder ............... A61P 37/02 435/328 |
| 2005/0249701 | A1 | 11/2005 | Morre et al. |
| 2006/0141581 | A1* | 6/2006 | Gillies ............... A61P 35/00 435/325 |
| 2008/0206190 | A1 | 8/2008 | Morre et al. |
| 2008/0300188 | A1* | 12/2008 | Yang ............... A61P 7/00 435/325 |
| 2010/0196312 | A1 | 8/2010 | Morre et al. |
| 2011/0243887 | A1 | 10/2011 | Lauder et al. |
| 2012/0016104 | A1 | 1/2012 | Morre et al. |
| 2013/0217864 | A1 | 8/2013 | Cho et al. |
| 2014/0178393 | A1 | 6/2014 | Andres et al. |
| 2014/0377218 | A1 | 12/2014 | Morre et al. |
| 2017/0158746 | A1* | 6/2017 | Yang ............... A61P 31/14 |

FOREIGN PATENT DOCUMENTS

| CN | 101687933 A | 3/2010 |
| CN | 108093638 A | 5/2018 |
| CN | 108778337 A | 11/2018 |
| EP | 0314415 B1 | 8/1994 |
| EP | 0877752 A1 | 11/1998 |
| JP | 2501618 B2 | 5/1996 |
| JP | 2000504220 A | 4/2000 |
| JP | 2001509661 A | 7/2001 |
| JP | 2009501543 A | 1/2009 |
| JP | 2010531134 A | 9/2010 |
| JP | 2014147396 A | 8/2014 |
| JP | 2015057392 A | 3/2015 |

(Continued)

OTHER PUBLICATIONS

Seo et al. Journal of Virology, 2014; 88(16):8998-9009 (Year: 2014).*
Bowie et al. Deciphering the Message in Protein Sequences: Tolerance to Amino Acid Substitutions. Science, 1990, 247: 1306-1310 (Year: 1990).*
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111:2129-2138, 1990 (Year: 1990).*

(Continued)

Primary Examiner — Vanessa L. Ford
Assistant Examiner — Sandra Carter
(74) Attorney, Agent, or Firm — Sterne, Kessler, Goldstein & Fox P.L.L.C.

(57) ABSTRACT

The present invention relates to a pharmaceutical composition comprising an interleukin-7 fusion protein to which an immunoglobulin Fc region has been fused for preventing or treating diseases caused by influenza virus A. The fusion protein comprising the immunoglobulin Fc region and IL-7 according to the present invention protects the body from infection due to influenza virus A and thus can treat diseases which can be caused by the virus.

17 Claims, 11 Drawing Sheets

Specification includes a Sequence Listing.

(56) References Cited

FOREIGN PATENT DOCUMENTS

| KR | 20060112673 | A  | 11/2006 |
|----|-------------|----|---------|
| KR | 20120041139 | A  | 4/2012  |
| KR | 20140004802 | A1 | 1/2014  |
| KR | 101380732   | B1 | 4/2014  |
| KR | 20170066265 | A  | 6/2017  |
| KR | 20090045953 | A  | 9/2020  |
| WO | WO-2004018681 | A2 | 3/2004 |
| WO | WO-2005021592 | A2 | 3/2005 |
| WO | WO-2007019232 | A2 | 2/2007 |
| WO | WO-2009101737 | A1 | 8/2009 |
| WO | WO-2015015516 | A2 | 2/2015 |

OTHER PUBLICATIONS

Lazar et al. Transforming Growth Factor alpha: Mutation of Aspartic Acid 47 and Leucine 48 Results in Different Biological Activities. Mol. Cell. Biol., 8:1247-1252, 1988 (Year: 1988).*
Bork. Powers and Pitfalls in Sequence Analysis: The 70% Hurdle. Genome Research, 2000; 10:398-400 (Year: 2000).*
Greenspan et al. 1999. Defining epitopes: It's not as easy as it seems; Nature Biotechnology, 17:936-937 (Year: 1999).*
Seo et al. Crucial roles of IL-7 in the development of T follicular helper cells and in the induction of humoral immunity. Journal of Virology, 2014; 88(16):8998-9009 (Year: 2014).*
Seo et al. Crucial roles of interleukin-7 in the development of T follicular helper cells and in the induction of humoral immunity. Journal of Virology, 2014; 88(16): 8998-9009 (Year: 2014).*
Seo, Y.B., et al., "Crucial roles of interleukin-7 in the development of T follicular helper cells and in the induction of humoral immunity," J. Virol. 88(16):8998-9009, American Society for Microbiology, United States (2014).
Kang, M.C., et al., "Intranasal Introduction of Fc-Fused Interleukin-7 Provides Long-Lasting Prophylaxis against Lethal Influenza Virus Infection," J. Virol. 90(5):2273-2284, American Society for Microbiology, United States (2016).
International Search Report and Written Opinion for International Application No. PCT/KR2016/013966, Korean International Property Office, mailed on Mar. 2, 2017, 13 pages.
Nam, H.J., et al., "Marked enhancement of antigen-specific T-cell responses by IL-7-fused nonlytic, but not lytic, Fc as a genetic adjuvant," Eur. J. Immunol. 40:351-358, Wiley-VCH, Germany (2010).
Fry, T.J., et al., "Interleukin-7: from bench to clinic," Blood 99(11):3892-3904, American Society for Hematology, United States (2002).
Genbank, "Interleukin-7 [synthetic construct]", Accession No. AAB70834.1, accessed at https://www.ncbi.nlm.nih.gov/protein/AAB70834.1, 1 page.
Heufler, C., et al., "Interleukin 7 Is Produced by Murine and Humane Keratinocytes," J. Exp. Med. 178(3):1109-1114, Rockefeller University Press, United States (1993).
International Search Report and Written Opinion for International Application No. PCT/KR2016/006214, Korean Intellectual Property Office, Korea, mailed Dec. 15, 2016, 16 pages.
International Preliminary Report on Patentability and Written Opinion for International Application No. PCT/KR2016/006214, Korean Intellectual Property Office, Korea, mailed Dec. 12, 2017, 11 pages.
Kroncke, R., et al., "Human follicular dendritic cells and vascular cells produce interleukin-7: a potential role for interleukin-7 in the germinal center reaction," Eur. J. Immunol. 26(10): 2541-2544, Wiley-VCH, Germany (1996).
Pellegrini, M., et al., "IL-7 Engages Multiple Mechanisms to Overcome Chronic Viral Infection and Limit Organ Pathology," Cell 144(4):601-613, Cell Press, United States (2011).
Muegge, K., et al., "Interleukin-7: A Cofactor for V(D)J Rearrangement of the T Cell Receptor B Gene," Science 261(5117):93-95, American Association for the Advancement of Science, United States (1993).
Nanjappa, S.G., et al., "Immunotherapeutic effects of IL-7 during a chronic viral infection in mice," Blood 117(19):5123-5132, American Society of Hematology, United States (2011).
Patel, A., et al., "Treatment of progressive multifocal leukoencephalopathy and idiopathic CD4+ lymphocytopenia," J. Antimicrob. Chemother. 65(12):2489-2492, Oxford University Press, United Kingdom (2010).
Pellegrini, M., et al., "Adjuvant IL-7 antagonizes multiple cellular and molecular inhibitory networks to enhance immunotherapies," Nat. Med. 15(5):528-536, Nature Portfolio, Germany (2009).
Mikayama, T., et al., "Molecular cloning and functional expression of a cDNA encoding glycosylation-inhibiting factor," Proc. Natl. Acad. Sci. USA 90(21):10056-10060, PNAS, United States (1993).
*Biochemistry*, Voet, D., et al., eds., pp. 126-128 and 228-234, John Wiley & Sons, Inc., United States (1990).
Rosenberg, S.A., et al., "IL-7 Administration to Humans Leads to Expansion of CD8+ and CD4+ Cells but a Relative Decrease of CD4+ T-Regulatory Cells," J. Immunother. 39(3):313-319, Lippincott Williams and Wilkins Ltd., United States (2006).
Sawa, Y., et al., "Hepatic Interleukin-7 Expression Regulates T Cell Responses," Immunity 30(3):447-457, Cell Press, United States (2009).
Snyder, K.M., et al., "IL-7 in allogeneic transplant: Clinical promise and potential pitfalls," Leuk. Lymphoma. 47(7):1222-1228, Informa, United Kingdom (2006).
Watanabe, M., et al., "Interleukin 7 Is Produced by Human Intestinal Epithelial Cells and Regulates the Proliferation of Intestinal Mucosal Lymphocytes," J. Clin. Invest. 95:2945-2953, American Society for Clinical Investigation, United States (1995).
Bork, P., "Powers and Pitfalls in Sequence Analysis: The 70% Hurdle," Genome Res. 10(4):398-400, Cold Spring Harbor Laboratory Press, United States (2000).
Communication in counterpart application No. EP16807859, European Patent Office, Germany mailed May 15, 2019, 1 page.
Partial European Search Report in counterpart application No. EP16807859, European Patent Office, Germany, mailed Dec. 19, 2018, 6 pages.
International Search Report in International Application No. PCT/KR2016/012495, Korean Intellectual Property Office, Korea, mailed Jan. 13, 2017, 4 pages.
Notice for Reasons of Refusal in counterpart application No. JP2017564121, Japanese Patent Office, Japan, mailed Jan. 8, 2019, 5 pages.
Protein Data Bank, "Crystal Structure of Recombinant Human IgG4 Fc," NCBI, accessed at https://www.rcsb.org/structure/4c54, Nov. 2013, 4 pages.
Whisstock, J.C., et al., "Prediction of protein function from protein sequence and structure," Q. Rev. Biophys. 36(3):307-340, Cambridge University Press, United Kingdom (2003).
International Search Report for International Application No. PCT/KR2016/014127, Korean Intellectual Property Office, Korea, mailed on Mar. 9, 2017.
Fazeli, M., et al., "Efficacy of HPV-16 E7 Based Vaccine in a TC-1 Tumoric Animal Model of Cervical Cancer," Cell Journal 12(4):483-488, Cell Press, United States (2011).
Bowie, J.U., et al., "Deciphering the message in protein sequences: tolerance to amino acid substitutions," Science 247:1306-1310, American Association for the Advancement of Science, United States (1990).
Burgess, W.H., et al., "Possible dissociation of the heparin-binding and mitogenic activities of heparin-binding (acidic fibroblast) growth factor-1 from its receptor-binding activities by site-directed mutagenesis of a single lysine residue," J. Cell Biol. 111(5):2129-2138, Rockefeller University Press, United States (1990).
Lazar, E., et al., "Transforming growth factor alpha: mutation of aspartic acid 47 and leucine 48 results in different biological activities," Mol. Cell Biol. 8:1247-1252, Taylor & Francis, United States (1988).
Greenspan, N.S., et al., "Defining epitopes: It's not as easy as it seems," Nature Biotechnol. 17:936-937, Nature Publishing Group, United Kingdom (1999).

(56) References Cited

OTHER PUBLICATIONS

Choi, Y.W., et al., "ID: 80: Intravaginal Fc-fused IL-7 attract DNA vaccine-induced CD8 T cell in the genital tract," Cytokine 76(1):80, Elsevier, Netherlands (2015).

Huston, W.M., et al., "Vaccination to protect against infection of the female reproductive tract," Expert Rev. Clin. Immunol. 8(1):81-94, Taylor & Francis, United Kingdom (2012).

Gottlieb, S.L., et al., "Future prospects for new vaccines against sexually transmitted infections," Curr. Opin. Infect. Dis. 30(1):77-86, Wolters Kluwer, Switzerland (2017).

Genbank, "Ig gamma-2a chain (mAb735)—mouse," Accession No. S40295, published Jul. 16, 1000, accessed at https://www.ncbi.nim.nih.gov/protein/481974, 2 pages[KD2].

Genbank, "interleukin-1 receptor antagonist protein isoform 1 precursor [*Homo sapiens*]," Accession No. NP_776214.1, accessed at https://www.ncbi.nlm.nih.gov/protein/NP_776214.1/, 3 pages.

Taubenberger, J.K., et al., "Influenza: the once and future pandemic," Public Health Rep 125 Suppl 3:16-26, SAGE, United States (Apr. 2010).

Dunning, J., et al., "Antiviral combinations for severe influenza," Lancet Infect Dis 14(12):1259-70, Elsevier, United States (Dec. 2014).

Damjanovic, D., et al., "Immunopathology in influenza virus infection: uncoupling the friend from foe," Clinical Immunology, 144:57-69, Elsevier, Netherlands (Jul. 2012).

Kwon, D., et al., "Fc-fused IL-7 provides broad antiviral effects against respiratory virus infections through IL-17A-producing pulmonary innate-like T cells," Cell Rep Med 5(1): 101362 (Jan. 2024) ("Exhibit A").

\* cited by examiner

VIRUS INFECTION USING PHARMACEUTICAL COMPOSITION COMPRISING IMMUNOGLOBULIN Fc-FUSED INTERLEUKIN-7 FUSION PROTEIN

CROSS REFERENCE TO RELATED APPLICATIONS

This application is a continuation application of U.S. application Ser. No. 15/777,437 (currently allowed), which is a U.S. National Stage of International Application No. PCT/KR2016/013966, filed on Nov. 30, 2016, which claims the priority benefit of U.S. Provisional Application No. 62/263,262, filed on Dec. 4, 2015, each of which is hereby incorporated by reference in its entirety.

REFERENCE TO SEQUENCE LISTING SUBMITTED ELECTRONICALLY VIA EFS-WEB

The content of the electronically submitted sequence listing in ASCII text file (Name: 4241.0340005_Seqlisting_ST25.txt; Size: 75,273 bytes; and Date of Creation: Jun. 13, 2022) filed with the application is incorporated herein by reference in its entirety.

TECHNICAL FIELD

The present invention relates to a composition of a fusion protein comprising interleukin-7 for preventing or treating viral infection, and more particularly, to a pharmaceutical composition which can be used for preventing or treating influenza virus infection comprising an interleukin-7 fusion protein in which immunoglobulin Fc region is fused.

BACKGROUND ART

Influenza A virus (IAV) is a seasonal epidemic virus which threatens human health. Recently, it has been reported that avian IAV variants including H5N1 and H7N9 can cross-infect humans with higher mortality than other strains of human-infecting IAV. In case of the avian IAV variants, no human-to-human transmission has been reported, but new IAV variants are likely to occur in humans without pre-existing immunity to the viral variant, which is a risk factor for the outbreak of global epidemic (Taubenberger J K et al., 2010, *Public Health Rep* 125 Suppl 3:16-26).

Although vaccinations against influenza virus are conducted every year, such vaccines have problems such as low productivity and low efficacy. In other words, it is very difficult to timely produce vaccines against new antigens found in mutant viruses.

Antiviral drugs such as a neuraminidase inhibitor, influenza virus therapeutic agent, have been reported to slow the progression of complications. In particular, it has been reported that treatment with a neuraminidase inhibitor within 2 to 3 days after IAV infection is effective in treating IAV (Dunning J et al., 2014, *The Lancet infectious diseases* 14:1259-1270). However, owing to the emergence of new viral variants resistant to antiviral drugs, one antiviral drug alone cannot prevent or treat all viral infections. Therefore, an effective countermeasure for highly pathogenic IAVs is urgently needed.

Accordingly, the present inventors have endeavored to develop a therapeutic agent capable of effectively inducing an immune response in vivo regardless of the mutation of the virus, and as a result, have found that an interleukin-7-Fc fusion protein has an excellent effect for the prevention and treatment of highly pathogenic influenza virus to complete the present invention.

DISCLOSURE OF INVENTION

Technical Problem

An object of the present invention is to provide a composition for preventing or treating a disease caused by influenza virus.

Solution to Problem

In accordance with one object of the present invention, there is provided a pharmaceutical composition for preventing or treating a disease caused by influenza virus, comprising an interleukin-7 (IL-7) fusion protein in which immunoglobulin Fc region is fused.

In accordance with another object of the present invention, there is provided a method for preventing or treating a disease caused by influenza virus, comprising administering to an individual an interleukin-7 (IL-7) fusion protein in which immunoglobulin Fc region is fused and a pharmaceutically acceptable carrier.

Advantageous Effects of Invention

A fusion protein comprising immunoglobulin Fc region and IL-7 according to the present invention can control the immune system in the individual to protect human body from infection by influenza virus, and also, the fusion protein can control immune-related substances to treat a disease caused by the virus. Accordingly, it can be utilized as a new pharmaceutical composition which can replace the conventional antiviral vaccine.

BEST MODE FOR CARRYING OUT THE INVENTION

Figure 1A:
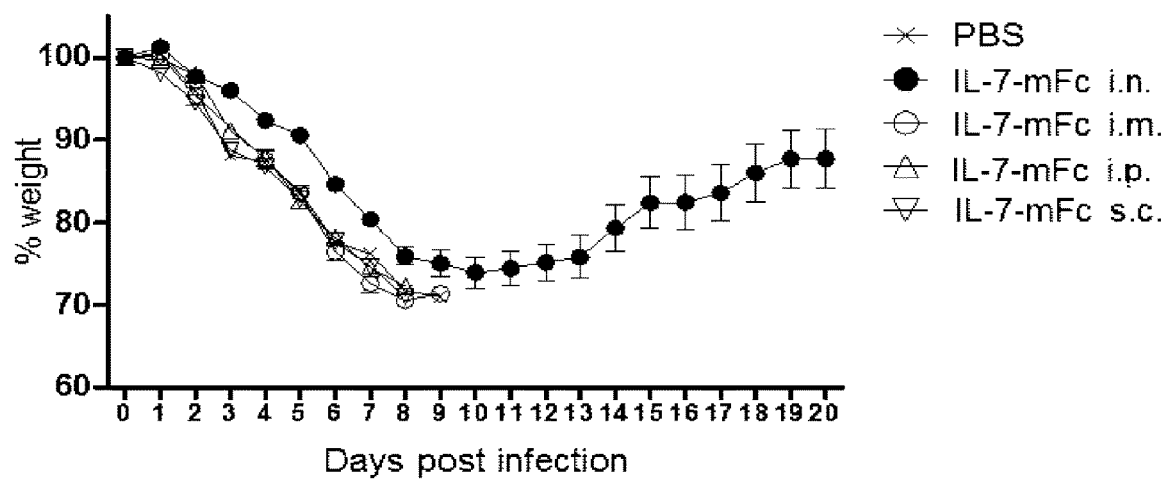
FIGS. 1a and 1b are graphs respectively showing weight change rate with respect to their initial body weight and survival rate of BALB/c mice depending on time passage after administration of IL-7-mFc through different routes.

In one aspect, the present invention provides a pharmaceutical composition for preventing or treating a disease caused by influenza virus, comprising an interleukin-7 (IL-7) fusion protein in which immunoglobulin Fc region is fused.

As used herein, the term "interleukin-7" may be a protein having the same amino acid sequence as interleukin-7 derived from an animal or a human. Further, the term "interleukin-7" may be a polypeptide or a protein having an activity similar to the interleukin-7 derived in vivo. Specifically, the IL-7 may be a protein comprising an IL-7 protein or a fragment thereof. Also, the IL-7 may be derived from a human, a rat, a mouse, a monkey, cattle or sheep.

The IL-7 comprises a polypeptide consisting of the amino acid sequences represented by SEQ ID NO: 1 to SEQ ID NO: 6. In addition, the IL-7 may have homology of about 70%, 75%, 80%, 85%, 90%, 91%, 92%, 93%, 94%, 95%, 96%, 97%, 98%, 99% or more to the sequences of SEQ ID NO: 1 to SEQ ID NO: 6.

Specifically, human IL-7 may have an amino acid sequence represented by SEQ ID NO: 1 (Genbank Accession No. P13232); rat IL-7 may have an amino acid sequence represented by SEQ ID NO: 2 (Genbank Accession No. P56478); mouse IL-7 may have an amino acid sequence represented by SEQ ID NO: 3 (Genbank Accession No. P10168); monkey IL-7 may have an amino acid sequence represented by SEQ ID NO: 4 (Genbank Accession No. NP_001279008); bovine IL-7 may have an amino acid sequence represented by SEQ ID NO: 5 (Genbank Accession No. P26895); and sheep IL-7 may have an amino acid sequence represented by SEQ ID NO: 6 (Genbank Accession No. Q28540).

In addition, the IL-7 protein or a fragment thereof may comprise a variety of modified proteins or peptides, i.e., variants. Such modification may be carried out by substitution, deletion or addition of one or more proteins of wild-type IL-7, which does not alter the function of IL-7. These various proteins or peptides may have homology of 70%, 75%, 80%, 85%, 90%, 91%, 92%, 93%, 94%, 95%, 96%, 97%, 98%, or 99% to a wild-type protein.

In general, substitution of a wild-type amino acid residue can be accomplished by substituting alanine or a conservative amino acid that does not affect the charge, polarity, or hydrophobicity of the entire protein.

The term "IL-7 protein" as used in the specification may be used as a concept including "IL-7 protein" and a fragment thereof. The terms "protein," "polypeptide," and "peptide" may be used interchangeably, unless otherwise specified.

In addition, the IL-7 may be a modified IL-7 having the following structure:

A-IL-7, wherein said A is an oligopeptide consisting of 1 to 10 amino acid residues, and the IL-7 is an interleukin-7 or a polypeptide having the activity similar to the interleukin-7.

Herein, said A may be directly linked to the N-terminus of the IL-7 or may be linked through a linker.

Said A may increase the productivity of IL-7 and may be prepared according to the method disclosed in Korean Patent Application No. 10-2016-0072769.

As used herein, said A may be linked to the N-terminus of IL-7. In the above formula, said A is characterized by containing 1 to 10 amino acids, which may be preferably selected from the group consisting of methionine, glycine, serine, and a combination thereof.

It is known that methionine and glycine do not induce an immune response in the human body. Although various protein therapeutic agents produced from E. coli necessarily contain methionine at the N-terminus thereof, no adverse immune effect has been reported. In the meantime, glycine is widely used in GS linker, and it is known that a commercial product such as Dulaglutide does not induce an immune response.

According to one embodiment, the oligopeptide A may be an oligopeptide comprising 1 to 10 amino acids selected from the group consisting of methionine (Met, M), glycine (Gly, G) and a combination thereof. Preferably the oligopeptide A may be an oligopeptide consisting of 1 to 5 amino acids. For example, the oligopeptide may be represented by the amino acid sequence selected from the group consisting of methionine, glycine, methionine-methionine, glycine-glycine, methionine-glycine, glycine-methionine, methionine-methionine-methionine, methionine-methionine-glycine, methionine-glycine-methionine, glycine-methionine-methionine, methionine-glycine-glycine, glycine-methionine-glycine, glycine-glycine-methionine and glycine-glycine-glycine. Herein, the modified IL-7 may have any one of the amino acid sequences selected from SEQ ID NOS: 15 to 20.

Further, immunoglobulin Fc region may comprise an animal or human immunoglobulin Fc region, or a modified immunoglobulin Fc region thereof.

The IL-7 may be linked to the N-terminus or the C-terminus of the Fc region. It is known that even when IL-7 is fused to the C-terminus of the Fc region, IL-7 activity is maintained (U.S. Pat. No. 8,338,575 B2).

As used herein, the term "Fc region," "Fc fragment" or "Fc" refers to a protein which comprises heavy chain constant region 2 (CH2) and heavy chain constant region 3 (CH3) of immunoglobulin but does not comprise variable regions of heavy or light chain and light chain constant region 1 (CL1). It may further comprise a hinge region of the heavy chain constant region. Hybrid Fc or a hybrid Fc fragment may herein also be referred to as "hFc" or "hyFc." Also, as used herein, the term "a modified immunoglobulin Fc region" or "Fc region variant" refers to the Fc region in which one or more amino acids in the Fc region are substituted or the Fc region which is prepared by combining different Fc regions. Preferably, it refers to a Fc region whose binding force with a Fc receptor and/or a complement has been modified so as to exhibit weakened antibody-dependent cell-mediated cytotoxicity (ADCC) or complement dependent cytotoxicity (CDC) compared to the wild-type Fc region. The modified immunoglobulin Fc region can be selected from the group consisting of IgG1, IgG2, IgG3, IgD, IgG4, and a combination thereof.

In particular, the modified immunoglobulin Fc region comprises CH2 domain and CH3 domain in the N-terminus to C-terminus direction, wherein the CH2 domain comprises a portion of an amino acid residue of CH2 domain of human IgD and human IgG4, and the CH3 domain comprises a portion of an amino acid residue of human IgG4 CH3 domain.

The Fc region variant can be modified so as to increase the stability of the hinge region. Specifically, the $144^{th}$ amino acid and/or the $145^{th}$ amino acid of SEQ ID NO: 9 can be modified. Preferably, the variant may be a mutant in which K, the $144^{th}$ amino acid of SEQ ID NO: 9, is substituted by G or S, and E, the $145^{th}$ amino acid, is substituted by G or S.

In addition, the hFc can be represented by the following formula (I):

$$N'\text{---}(Z1)p\text{-}(Y)q\text{-}Z2\text{-}Z3\text{-}Z4\text{-}C', \quad \text{[Formula (I)]}$$

wherein,
N' is the N-terminus of a polypeptide and C' is the C-terminus of the polypeptide,
p or q is an integer of 0 or 1,
Z1 is an amino acid sequence having 5 to 9 consecutive amino acid residues in the N-terminus direction from the $98^{th}$ position in the amino acid residues at $90^{th}$ to $98^{th}$ positions of SEQ ID NO: 7,
Y is an amino acid sequence having 5 to 64 consecutive amino acid residues in the N-terminus direction from the $162^{nd}$ position in the amino acid residues at $99^{th}$ to $162^{nd}$ positions of SEQ ID NO: 7,
Z2 is an amino acid sequence having 4 to 37 consecutive amino acid residues in the C-terminus direction from the $163^{rd}$ position in the amino acid residue at positions $163^{rd}$ to $199^{th}$ in SEQ ID NO: 7,
Z3 is an amino acid sequence having 71 to 106 consecutive amino acid residues in the N-terminus direction from the $220^{th}$ position in the amino acid residues at $115^{th}$ to $220^{th}$ positions of SEQ ID NO: 8, and
Z4 is an amino acid sequence having 80 to 107 amino acid residues in the C-terminus direction from the $221^{st}$ position in the amino acid residues at $221^{st}$ to $327^{th}$ positions of SEQ ID NO: 8.

In addition, Fc fragment of the present invention may be a wild type sugar chain, an increased sugar chain compared with the wild type, a reduced sugar chain compared with the wild type, or a form in which the sugar chain is removed. The increase, reduction or removal of immunoglobulin Fc sugar chain can be carried out by a conventional method known in the art such as chemical method, enzymatic method and genetic engineering method using microorganisms. The removal of the sugar chain from Fc fragment rapidly reduces the binding affinity of the primary complement component C1 to C1q and results in a decrease or loss of ADCC (antibody-dependent cell-mediated cytotoxicity) or CDC (complement-dependent cytotoxicity), thereby not inducing unnecessary immune responses in vivo. In this regard, immunoglobulin Fc fragment in a deglycosylated or aglycosylated form may be more suitable for the purpose of the present invention as a carrier of a drug. As used herein, the term "deglycosylation" refers to enzymatical elimination of sugar from Fc fragment, and the term "aglycosylation" refers to the production of Fc fragment in an unglycosylated form by a prokaryote, preferably *E. coli*.

The modified immunoglobulin Fc region may comprise amino acid sequences of SEQ ID NO: 9 (hFc01), SEQ ID NO: 10 (hFc02), SEQ ID NO: 11 (hFc03), SEQ ID NO: 12 (hFc04) or SEQ ID NO: 13 (hFc05). In addition, the modified immunoglobulin Fc region may comprise the non-lytic mouse Fc of SEQ ID NO: 14.

According to the present invention, the modified immunoglobulin Fc region may be one described in U.S. Pat. No. 7,867,491, and the production of the modified immunoglobulin Fc region may be carried out with reference to the disclosure of U.S. Pat. No. 7,867,491.

In addition, the interleukin-7 fusion protein in which immunoglobulin Fc region is fused may have the amino acid sequence of any one of SEQ ID NOS: 21 to 27.

Meanwhile, the influenza virus may be Influenza A virus (IAV). In addition, the influenza A virus may have various kinds of H types and N types. The virus may specifically be one of 16 kinds of H subtypes and may be one of 9 kinds of N subtypes. For a specific example, the virus may be, but not limited to, H7N9, H5N1, H5N2, H3N2 or H1N1.

The interleukin-7 fusion protein in which immunoglobulin Fc region is fused according to the present invention may further comprise a pharmaceutically acceptable carrier. The pharmaceutically acceptable carrier may be any carrier that is suitable for being delivered to a patient and is non-toxic to the patient. Distilled water, alcohol, fats, waxes and inert solids may be included as carriers. Pharmacologically acceptable adjuvant (a buffer or a dispersant) may also be included in the pharmacological composition.

In another aspect of the present invention, there is provided a method for preventing or treating a disease caused by influenza virus, comprising administering to an individual an interleukin-7 (IL-7) fusion protein in which immunoglobulin Fc region is fused and a pharmaceutically acceptable carrier.

Herein, the method of administration to an individual may be a local administration, preferably intranasal administration. In case of that the composition of the present invention is provided topically, such as intranasal or aerosol administration, the composition preferably comprises a portion of an aqueous or physiologically compatible body fluid suspension or solution. Accordingly, the carrier or vehicle may be physiologically acceptable, and thus it can be added to the composition and delivered to the patient, which does not adversely affect the electrolyte and/or volume balance of the patient. Thus, a carrier for a formulation may generally include physiologic saline.

The method for preventing or treating a disease using a fusion protein of the present invention or a composition comprising the same may comprise administering another drug or physiologically active substance having the effect of preventing or treating a disease in combination with the protein or the composition of the present invention, while the route, timing, and dosage of the co-administration may be determined depending on the type of a disease, disease condition of a patient, the purpose of treatment or prevention, and other drug or physiologically active substance co-administered.

The isolated nucleic acid molecule encoding the modified interleukin-7 or a fusion protein comprising the same may encode a polypeptide having an amino acid sequence selected from the group consisting of SEQ ID NOS: 15 to 25. The nucleic acid molecule may comprise a polynucleotide sequence selected from the group consisting of SEQ ID NOS: 29 to 39. The nucleic acid molecule may further comprise a signal sequence or a leader sequence.

MODE FOR THE INVENTION

Hereinafter, the present invention will be described in more detail with reference to the following examples. However, the following examples are for illustrative purposes only and are not intended to limit the scope of the present invention.

Preparation Example 1: Preparation of Experimental Animals

BALB/c, BALB/c-nude, C57BL/6, and FcRn$^{-/-}$ mice used in the following examples were purchased from the Jackson Laboratory (Bar Harbor, ME, USA) and raised under specific pathogen-free conditions in an approved animal facility at POSTECH Biotech Center and International Vaccine institute (Seoul, Korea). All mouse experiments were performed in accordance with National Institutes of Health guidelines, and protocols were approved by the Institutional Animal Care and Use Committee (IACUC).

Preparation Example 2: Preparation of Mice and Antibody Administration Method

The murine non-lytic Fc fused IL-7 and non-lytic Fc fragment were prepared (Kim E S et al., 2013, Nanoscale 5:4262-4269). Recombinant human IL-7 (IL-7) used in the following examples was purchased from Shenandoah Biotechnology (Warwick, PA, USA). A mixture of ketamine (100 mg/kg; Yuhan, Korea) and xylazine hydrochloride (10 mg/kg; Bayer, Belgium) in PBS was administered to the mice intraperitoneally to anesthetize, and then, 50 µl of PBS including predetermined cytokine was administered to the mice via indicated routes with a micropipette or syringe. The depletion monoclonal antibodies (mAbs) against mouse CD4 (GK1.5), CD8 (2.43), Vγ2 (UC3-10A6), and polyclonal rat IgG were purchased from Bioxcell (West Lebanon, NH, USA). 200 µg of each depletion mAb was administered to the mice intraperitoneally at -1, 0, 1, and 4 days of post-IAV infection.

Preparation Example 3: Virus Infection and Titration

Influenza strains H1N1 (A/Puertorico/8/34) and H5N2 (A/aquatic bird/ma81/2007) used in the following examples were kindly provided by Young Ki Choi from Chungbuk National University of Medicine (Korea). Mice adapted to H5N2 were generated by passaging the H5N2 (A/Aquatic bird/Korea/W81/05) (Song M S et al., 2009, *Journal of virology* 83:12325-12335). At the predetermined time point after IL-7-mFc treatment, mice were anesthetized and infected intranasally with 3 LD$_{50}$ of PR8 or H5N2. Experiments using H1N1 (A/California/04/09) and H3N2 (A/Philippines/2/82) were performed with the aid of International Vaccine Institute (Korea). Body weight change and survival were monitored daily and groups with more than 50% of dead mice were excluded from the body weight graph. Mice that lose weight more than 30% with respect to their initial body weight were euthanized.

To measure virus titers, total lung homogenate samples of 3 and 7 days after infection, which were diluted 4 times with ten-fold serial dilution, were added to a monolayer of Madin-Darby canine kidney (MDCK) cells and the cytopathic effects were monitored daily. Virus titer was determined by a hemagglutinin test and calculated by the Reed and Muench method (Kim E H et al., 2013, *Virology journal* 10:104). Virus titer was described as log$_{10}$ of the 50% tissue culture infective dose (TCID$_{50}$)/ml.

Preparation Example 4: BALF Collection and Lung Homogenate Preparation

The mice were anesthetized, and bronchoalveolar lavage fluid (BALF) was collected with 1 ml of PBS. After BALF collection, the lungs were collected and minced into small pieces and treated with type I collagenase (Gibco/Life Technology, Grand Island, NY, USA) and DNase I (Sigma-Aldrich, St. Louis, MO, USA) at 37° C. for 30 to 45 min. Tissue fragments were harvested and crushed through a 70-µm strainer (BD Biosciences/Falcon™, San Jose, CA, USA) to generate single cell suspensions. The cells were then washed and resuspended with RPMI-1640 (Welgene, Korea) containing 10% FBS (Hyclone, South Logan, UT, USA), 2-mercaptoethanol (Gibco), and antibiotics (Gibco).

Preparation Example 5: Quantification of Cytokines, Chemokines, Influenza-Specific Antibodies and Total Proteins in the BALF and Sera The levels of cytokines and chemokines were first identified with a milliplex MAP mouse cytokine/chemokine kit (Millipore, Billerica, MA, USA), and further analyzed using ELISA DuoSet kits (R&D systems, Minneapolis, MN, USA) for mouse IFN-γ, IL-6, G-CSF, MCP-1, and IP-10 according to the manufacturer's protocol. Total protein concentrations in the BALF were measured using protein assay dye reagent (Bio-Rad, Hercules, CA, USA) based on BSA (Roche, Germany) as a standard. To quantify the level of influenza-specific antibodies, total IgG and IgA were analyzed by direct ELISA with inactivated H5N2 virus. Total IgG-HRP and IgA-HRP were purchased from Southern Biotech (Birmingham, AL, USA).

Preparation Example 6: Flow Cytometry

To prevent non-specific antibody binding, the single-cell suspensions of lung homogenate were incubated with Fc-blocker (2.4G2; eBioscience, San Diego, CA, USA) in staining buffer (1% FBS in PBS). The cells were then stained with the following mAbs; mAbs against B220, CD3, CD4, CD8, CD11a, CD11b, CD11c, CD44, CD49d, CD62L, CD69, DX5, F4/80, Ly6C, MHC II, IFN-γ, TCRγδ, and 7-AAD (all from eBioscience); and mAbs against CD19, CD45, Gr-1, and Ly6G (all from BD Biosciences). For the intracellular cytokine staining of IFN-γ-producing CD8 T cells, lung homogenates were incubated for 6 hours with HA peptide (residue 529-543, Peptron, Korea), Brefeldin A (eBioscience) and DNase I (Sigma), and then stained using Cytofix/cytoperm in accordance with the manufacturer's protocol (BD Bioscience). All samples were analyzed with LSR Fortessa (BD Biosciences) and FlowJo software (Tree Star, St, Ashland, OR, USA).

Preparation Example 7: In Vivo Antibody Labeling

The mice were treated with PBS or 1 µg of IL-7-mFc intranasally. To analyze the pulmonary residency of T cells, at 7 and 14 days after IL-7-mFc treatment, 2.5 µg of anti-mouse CD3e-percp-cy5.5 (BD bioscience) was intravenously administered to the mice at 10 min prior to sacrifice (Anderson K G et al., 2014, *Nature protocols* 9:209-222). Residual antibody was removed by cardiac perfusion with PBS, and the lung resident T cell populations in single cell suspensions of lung homogenate were analyzed by flow cytometry.

Preparation Example 8: Histological Analysis and Inflammation Score Measurement

Mice were anesthetized, and the lungs were obtained via thoracotomy and transcardial perfusion with cold PBS. Perfused lungs were immediately fixed with 4% paraformaldehyde, kept at 4° C. overnight, and embedded into paraffin. Lung sections were then stained with hematoxylin and eosin solution (H&E, Sigma Aldrich). The images of whole lung tissues were captured with a Pannoramic MIDI slide scanner (3DHISTECH, Hungary). Pulmonary inflammation was assessed by the degree of peribronchiolar and perivascular inflammation (Choi J P et al., 2010, *Allergy* 65:1322-1330).

Preparation Example 9: mRNA Preparation, cDNA Synthesis, and Quantitative PCR Analysis of Lung Homogenate After preparation of lung homogenate, mRNAs were prepared with a Reliaprep™ mRNA preparation kit (Promega, Fitchburg, WI, USA), and cDNAs were synthesized with GoScript™ Reverse Transcriptase System (Promega) according to the manufacturer's protocol. Quantitative PCR assay was performed using Power SYBR Green Master Mix (Applied Biosystems, Foster City, CA). The following primers for qPCR analysis were synthesized by Genotech (Korea): NS-1 forward, TGCGGGAAAGCAGATAGTGG (SEQ ID NO: 41); NS-1 reverse, TCAGTTAGGTAGCGCGAAGC (SEQ ID NO: 42); L32 forward, GAAACTGGCGGAAACCCA (SEQ ID NO: 43); L32 reverse, and GGATCTGGCCCTTGAACCTT (SEQ ID NO: 44). Relative expression levels of H5N2 NS-1 mRNA were normalized to the level of L32 mRNA.

Preparation Example 10: Statistical Analysis Method

A two-tailed Student's t-test (*, $p<0.05$; , $p<0.01$) was used to evaluate the differences between two groups. A one-way ANOVA with Bonferroni's post-test (, $p<0.01$) was used for more than three groups. Differences in survival rates between groups were determined by a log-rank test (t, $p<0.05$; ††, $p<0.01$).

Example 1: Confirmation of Protective Effect of IL-7 Against IAV Infection and Pathway Dependence BALB/c mice (n=8/group) were treated with 1 μg of IL-7-mFc via various routes such as intranasal (i.n.), intramuscular (i.m.), intraperitoneal (i.p.) and subcutaneous (s.c.) routes, and then infected with 3 $LD_{50}$ of mouse adaptive avian influenza (H5N2, A/Aquatic bird/Korea/ma81/2005) after 2 weeks of IL-7-mFc treatment. The results are shown in FIGS. 1a and 1b.

Figure 1B:
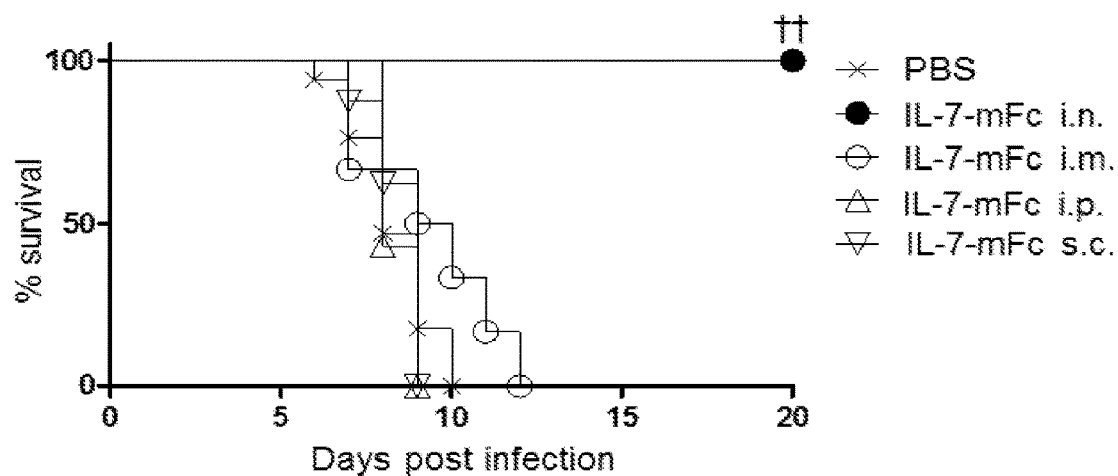

As shown in FIGS. 1a and 1b, intranasal IL-7-mFc treatment completely protected mice against lethal influenza infection, whereas IL-7-mFc treatment via an intramuscular, intraperitoneal and subcutaneous route showed no significant protection. These results reveal that induction of local immune responses by IL-7-mFc at the pathogen entry site, namely, the airway mucosa, may be critical for the protection against lethal IAV infection.

Example 2: Confirmation of Effective Dosage of IL-7-mFc Against IAV Infection and Function of Fc Fusion of IL-7

BALB/c mice (n=6/group) were treated with various ranges of doses among 0.04 μg to 10 μg of IL-7-mFc and 1 μg to 10 μg of recombinant human IL-7 (rhIL-7), and after 14 days, the mice were infected with 3 $LD_{50}$ of H5N2.

Figure 2A:
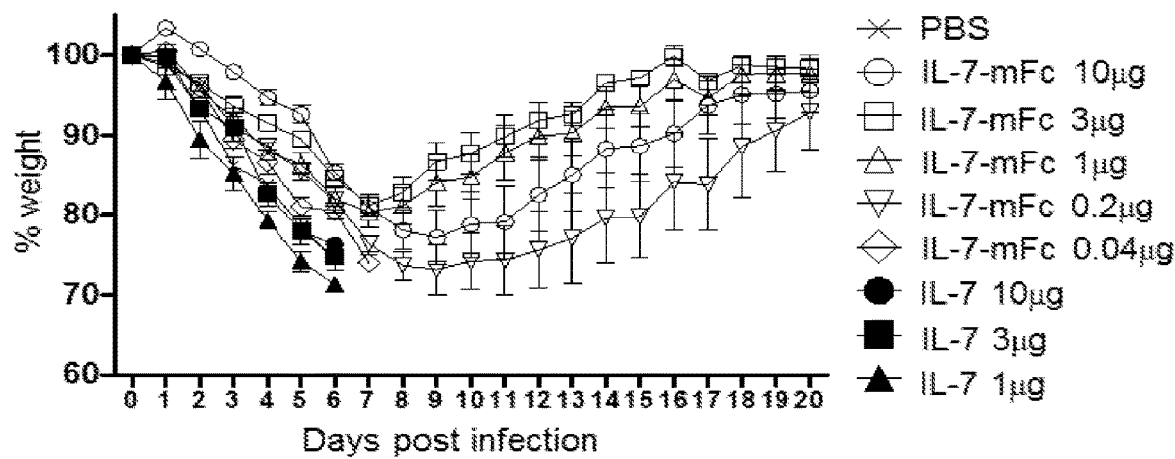
FIGS. 2a and 2b are graphs respectively showing weight change rate with respect to their initial body weight and survival rate of BALB/c mice depending on time passage after intranasal administration of IL-7-mFc and IL-7, respectively, with various doses.
Figure 2B:
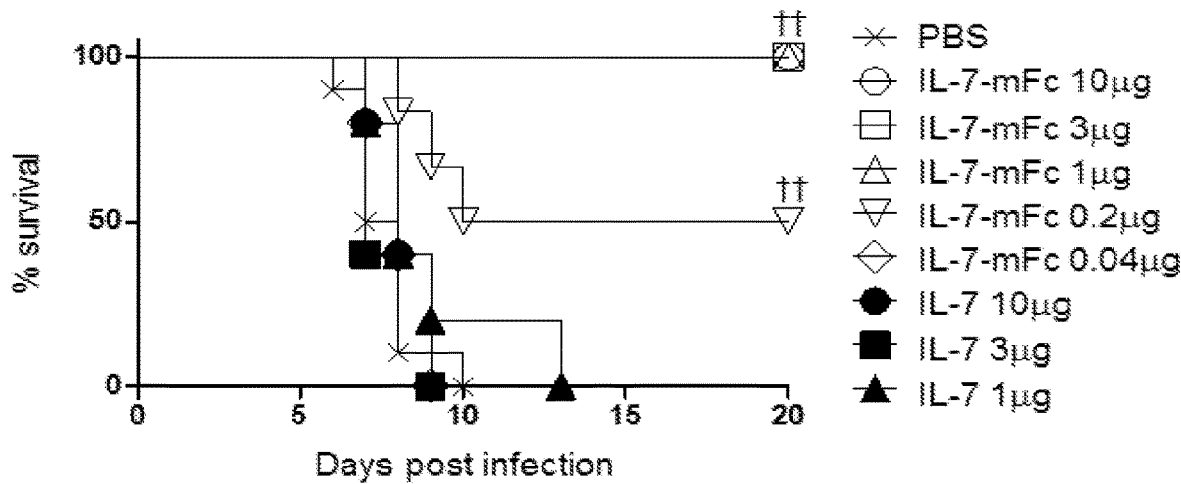

As a result, as shown in FIGS. 2a and 2b, no protection against IAV infection was observed in the mice treated with 0.04 μg of IL-7-mFc. In the mice treated with 0.2 μg of IL-7-mFc, 50% survival rate and partial protection against IAV were observed. In the mice treated with 1 μg, 3 μg, and 10 μg, i.e., 1 μg or more of IL-7-mFc dose, 100% survival rate and complete protection against IAV were observed. On the other hand, no protection against IAV was observed when 1 μg or more of rhIL-7 without Fc fusion was administered (1 μg, 3 μg and 10 μg).

In addition, BALB/c mice (n=6-8/group) were respectively treated with 1 μg of IL-7-mFc and 1 μg of Fc fragment (for comparison), at 14 days before IAV infection. After infection with 3 $LD_{50}$ of H5N2, the weight change with respect to the initial body weight and survival rate of the mice were observed for 20 days.

Figure 2C:
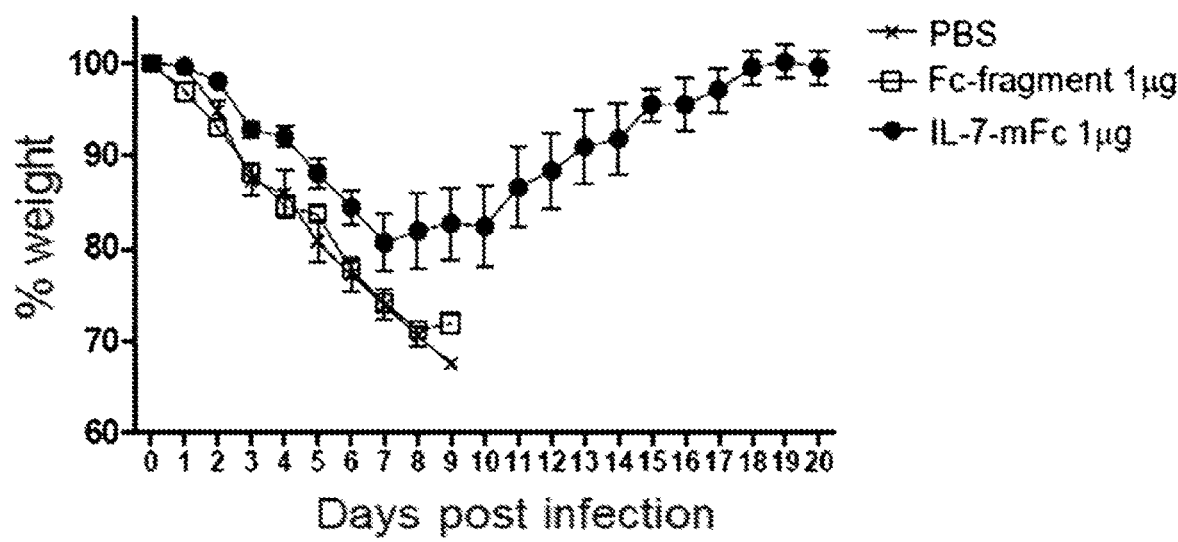
FIGS. 2c and 2d are graphs respectively showing weight change rate with respect to their initial body weight and survival rate of BALB/c mice depending on time passage after administration of 1 μg of IL-7-mFc and Fc-fragment, respectively.
Figure 2D:
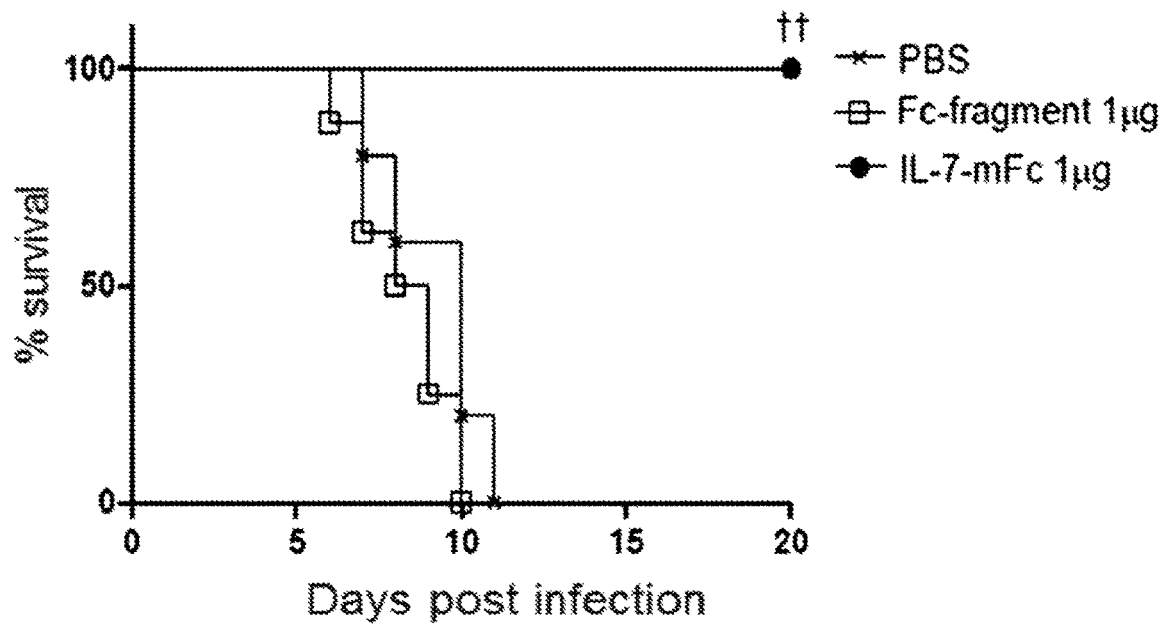

As a result, as shown in FIGS. 2c and 2d, 100% survival rate was observed in the mice treated with 1 μg of IL-7-mFc, whereas no protection was observed in the mice treated with 1 μg of Fc fragment.

These results confirm that the effective dose of IL-7-mFc for complete protection from IAV infection in mice is 1 μg or more. It was also found that Fc fragment alone did not have protection function against IAV infection.

Example 3: Confirmation of the Relationship Between FcRn and the Protective Effect Against IAV Infection PBS and 1 g of IL-7-mFc, were intranasally administered to C57BL/6 and FcRn$^{-/-}$ (neonatal Fc receptor-deficient) mice (n=8/group), and after 14 days, mice were infected with 3 $LD_{50}$ of H5N2 viruses.

Figure 3A:
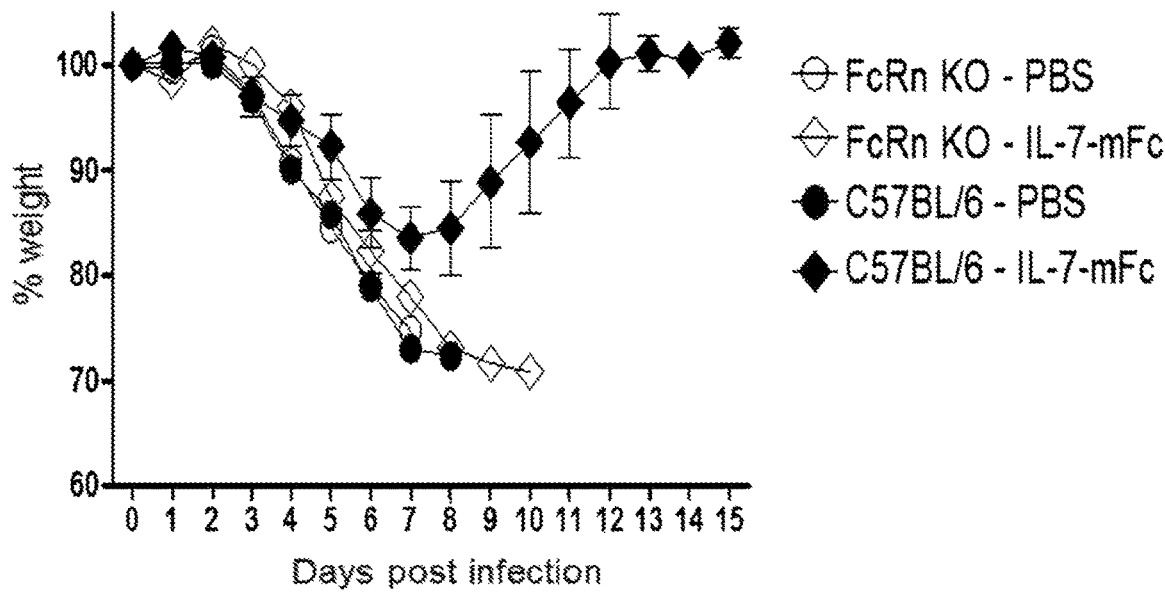
FIGS. 3a and 3b are graphs respectively showing weight change rate with respect to their initial body weight and survival rate of C57BL/6 and FcRn$^{-/-}$ mice depending on time passage after administration of PBS and 1 μg of IL-7-mFc, respectively.
Figure 3B:
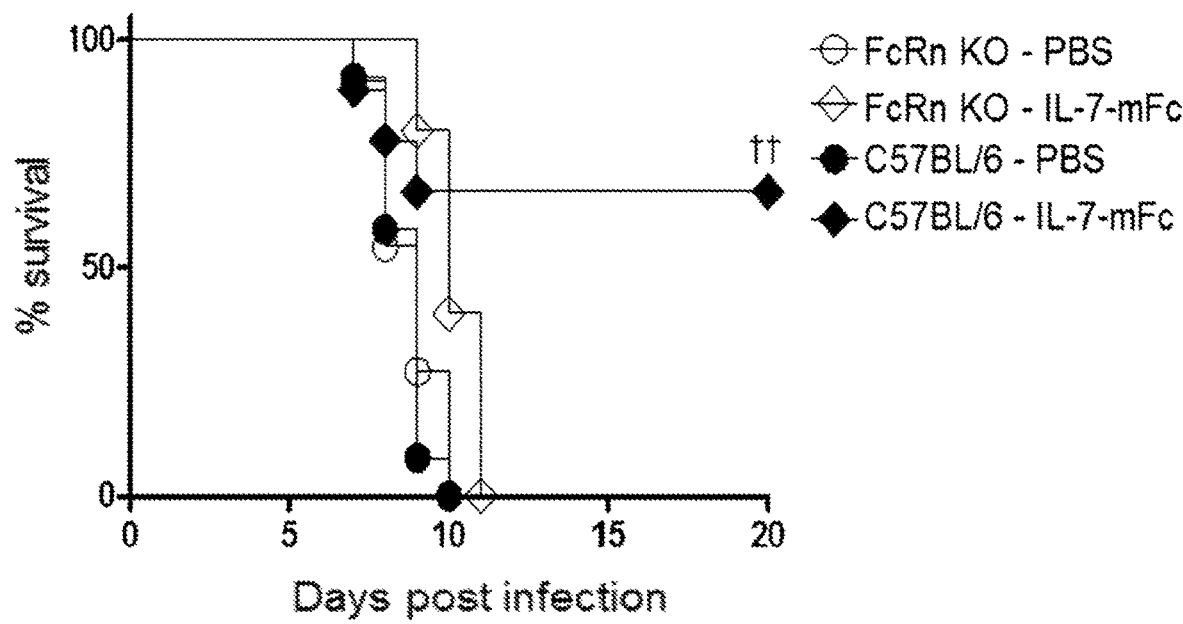

As a result, as shown in FIGS. 3a and 3b, none of the PBS-administered C57BL/6 and FcRn$^{-/-}$ mice showed any protection against IAV infection. Among the IL-7-mFc-treated mice, C57BL/6 mice showed protection against infection, whereas no protection against IAV infection was observed in FcRn$^{-/-}$ mice.

These results indicate that the protective immune response of the IL-7-Fc fusion protein arised from FcRn-dependent mechanism (transcytosis).

Example 4: Confirmation of Long-Term Protection Effect of IL-7-Fc Fusion Protein Against Lethal IAV Infections BALB/c mice (n=11/group) were infected with 3 $LD_{50}$ of H5N2 at 0, 3, 7, 14, 21 or 35 days after intranasal administration of 1 μg of IL-7-mFc.

Figure 4A:
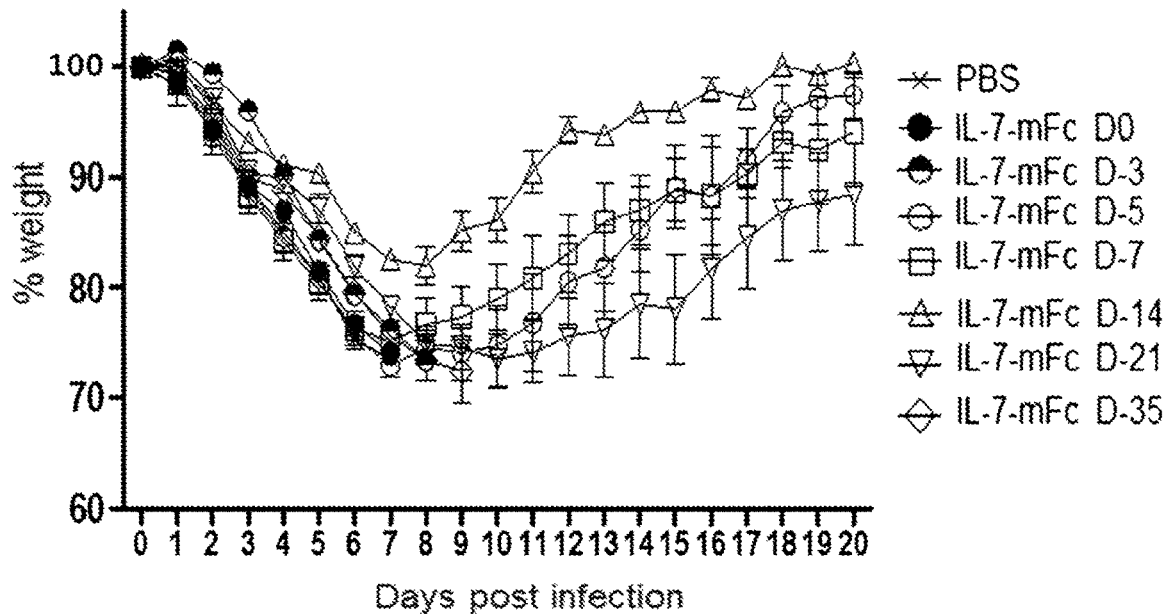
FIGS. 4a and 4b are graphs respectively showing weight change rate with respect to their initial body weight and survival rate of BALB/c mice depending on time passage at day 0, 3, 5, 7, 14, 21 or 35 after intranasal administration of 1 μg of IL-7-mFc.
Figure 4B:
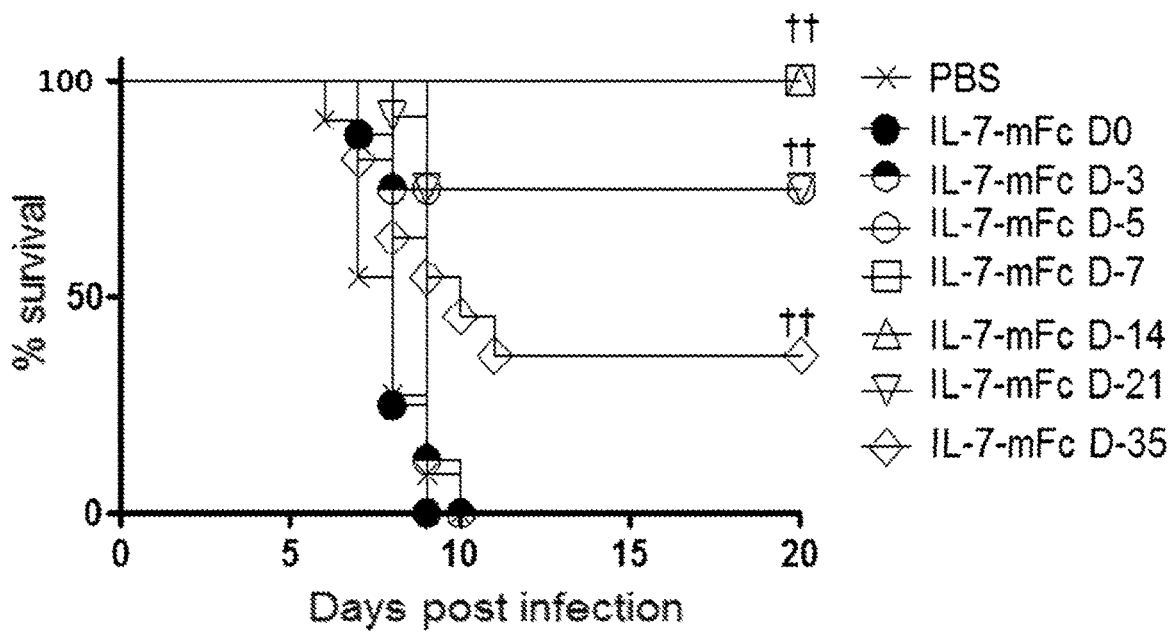
Figure 5A:
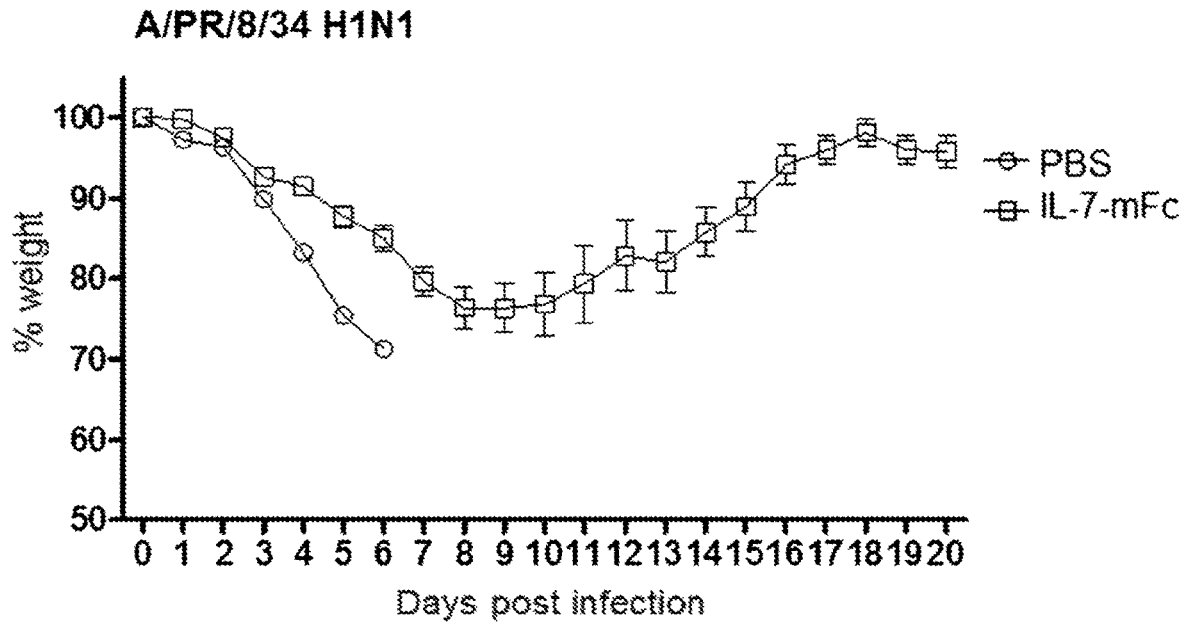
FIGS. 5a to 5f are graphs showing weight change rate with respect to their initial body weight and survival rate of BALB/c mice depending on time passage after infection with a lethal dose of A/PR/8/34 H1N1, A/California/04/09 H1N1 or A/Philippines/2/82 H3N2 at 14 days post-intranasal administration of IL-7-mFc.
Figure 5B:
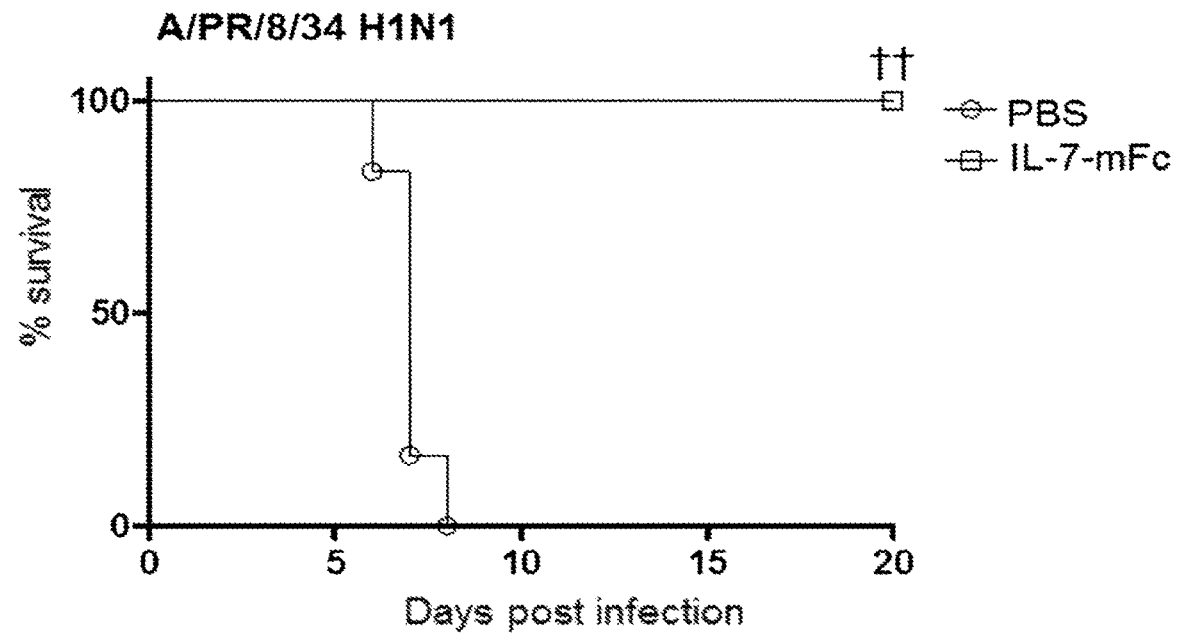
Figure 5C:
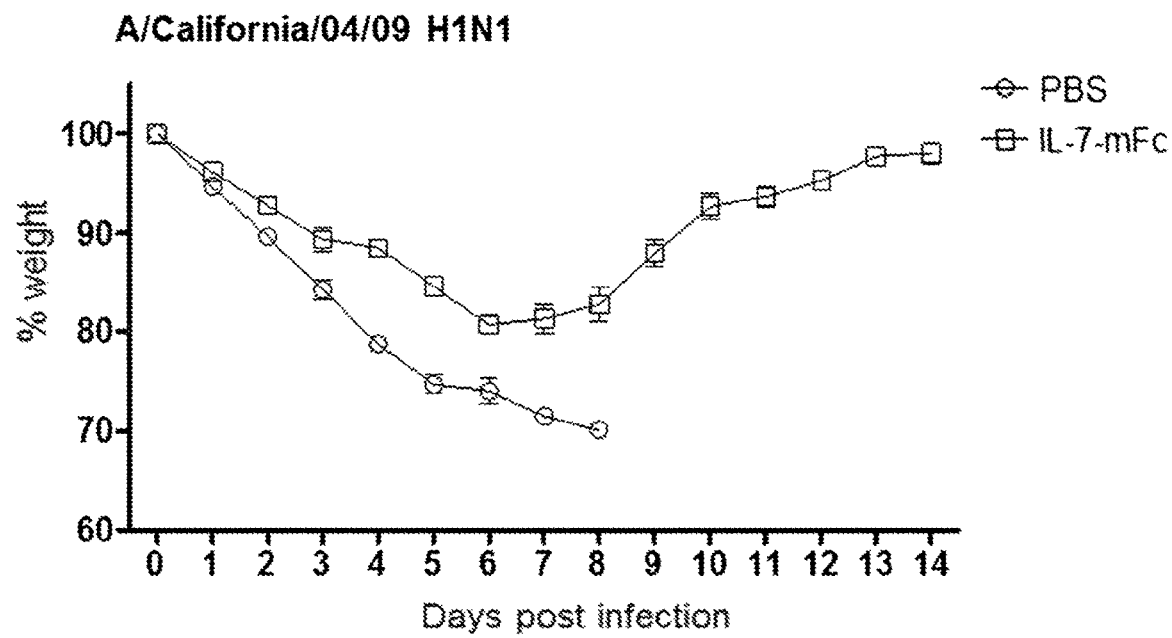
Figure 5D:
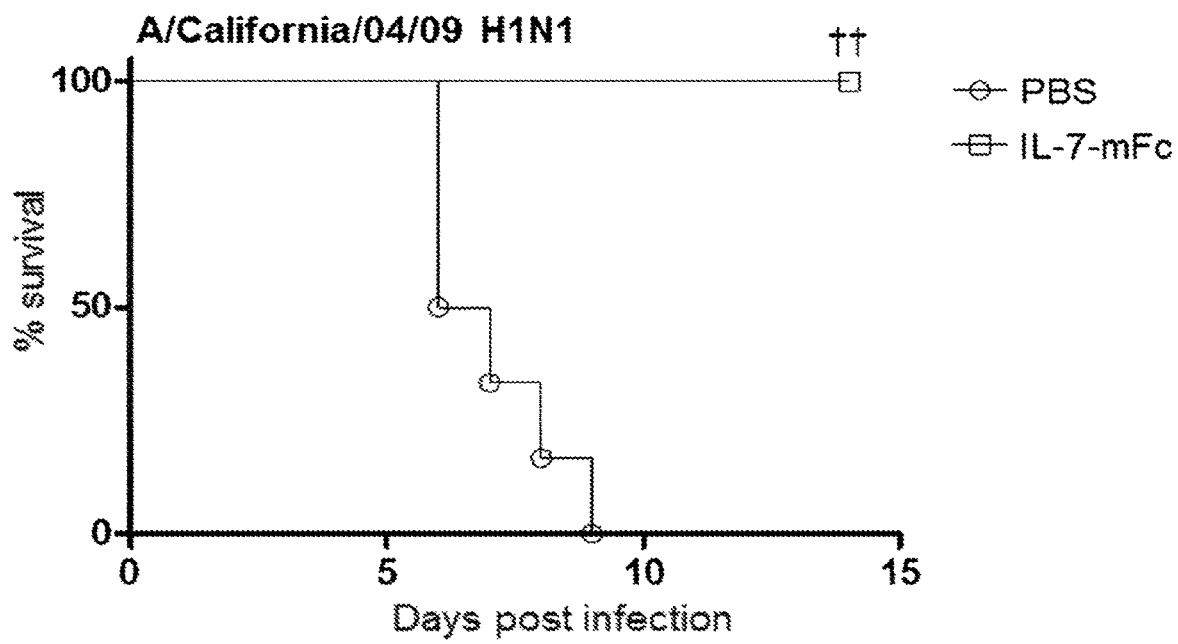
Figure 5E:
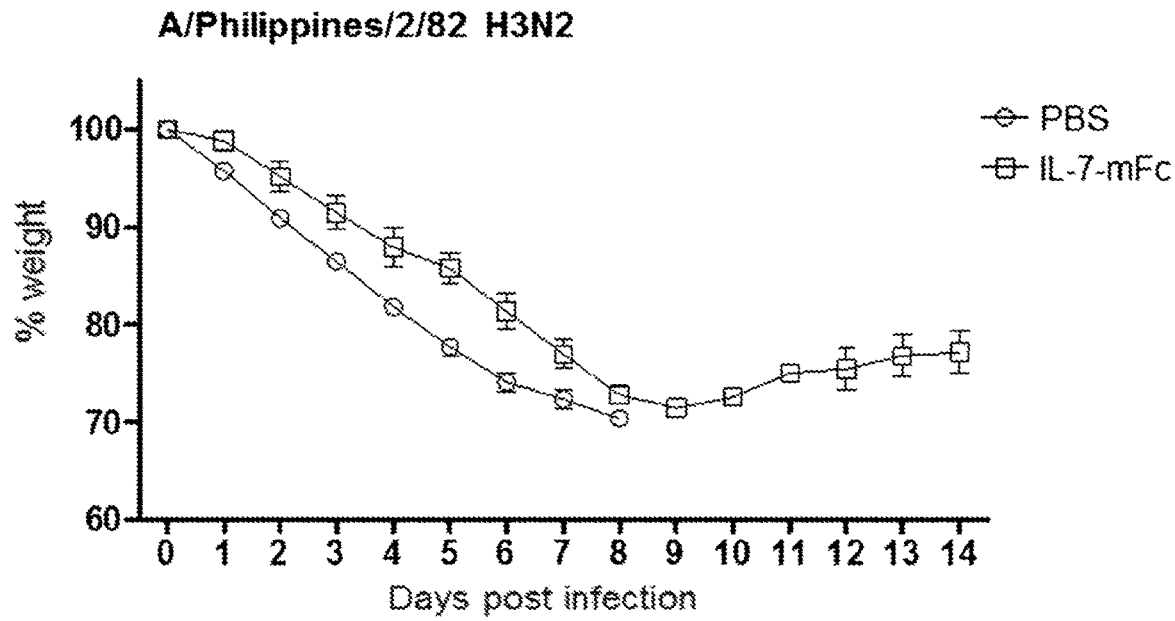
Figure 5F:
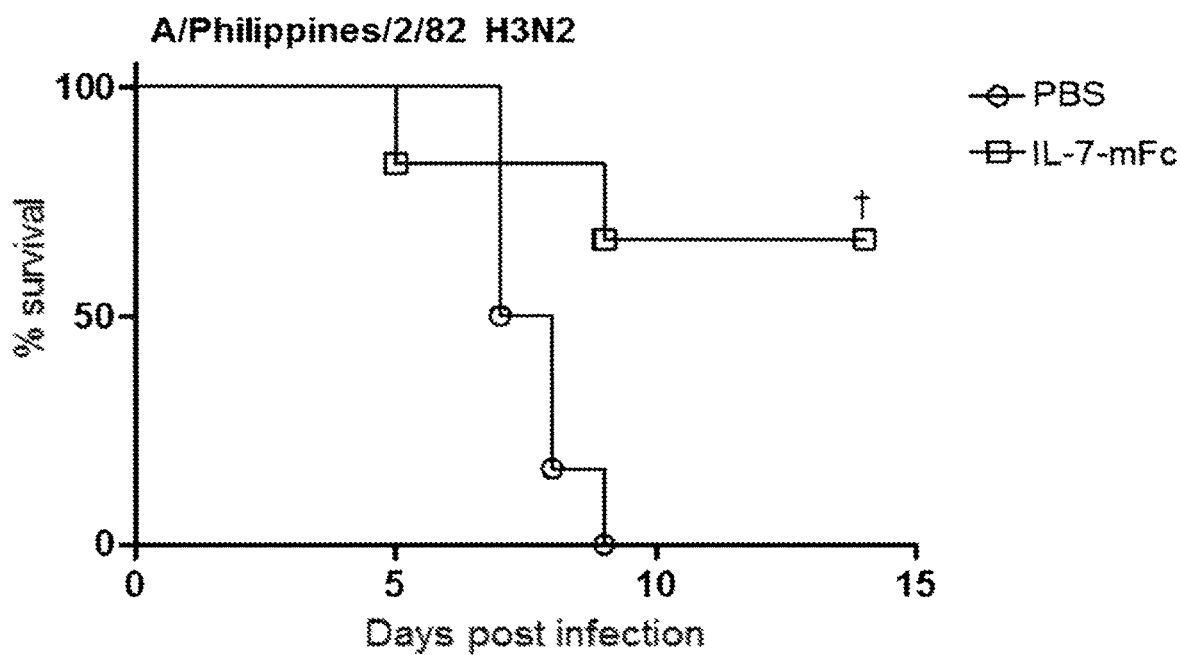

As a result, as shown in FIGS. 4a and 4b, the protective effect of IL-7-mFc was observed at 5 days after IL-7-mFc treatment, but no protective effect was observed at days 0 to 3. Complete protection against IAV was observed at 7 days and even at 14 days after IL-7-mFc treatment. This protective effect diminished over time but 63% and 36% of mice survival rate were found at 21 days and 35 days after IL-7-mFc treatment, respectively.

These results indicate that the protective effect of IL-7-mFc against IAV infection persists from 5 to 35 days after IL-7-mFc treatment.

Example 5: Confirmation of the Protective Effect of the IL-7-Fc Fusion Protein Against the Variant Virus BALB/c mice (n=6/group) were infected with lethal doses of IAV varians of H1N1 (A/Puerto Rico/8/34 and A/California/04/09) and H3N2 (A/Philippines/2/82) at 14 days after IL-7-mFc nasal administration. The mean weight loss was shown as the percentage relative to the initial weight at the time of infection (mean±SEM) and the survival rate was analyzed by the Kaplan-Meier method. The protective effects of IL-7-mFc against infection of H1N1 (A/Puerto Rico/8/34), H1N1 (A/California/04/09) and H3N2 (A/Philippines/2/82) are shown in FIGS. 5a to 5f.

As shown in FIGS. 5a to 5f, all mice pretreated with IL-7-mFc at 14 days before infection with H1N1 (A/Puerto Rico/8/34), H1N1 (A/California/04/09) and H3N2 (A/Philippines/2/82) showed protective effect.

These results indicate that IL-7-Fc fusion protein effectively induces local immune response regardless of the mutation of the virus, thereby improving the survival rate.

Example 6: Evaluation of Effect of IL-7-Fc Fusion Protein on Pulmonary T Cells The numbers of lymphocytes in the lung tissues were analyzed at 0, 3, 7, 14, 21, and 35 days after intranasal administration of 1 μg of IL-7-mFc to the mice. At each point, the absolute numbers of immune cells in the total lung homogenate were calculated based on the percentage of the total cells by flow cytometry. The results shown in Table 1 were expressed as the mean±SEM of four mice/group (N.D., not determined; *, $p<0.05$; **, $p<0.01$ by Student's t test compared with cell numbers on day 0 (Table 1)). The expression of CD11a and CD49d in lung CD4 and CD8 T cells of BALBb/c (n=4) mice with $CD62L^{high}CD44^{low}$ and $CD62L^{low}CD44^{high}$ phenotypes to which IL-7-mFc had been administered was analyzed by flow cytometry.

Example 7: In Vivo Antibody Labelling Experiment to Confirm that Pulmonary T Cells are Lung-Retentive BALB/c mice were sacrificed at 7 days after intranasal administration of PBS and IL-7-mFc. 10 minutes prior to sacrifice, 2.5 μg of CD3 mAb-conjugated Percp-Cy5.5 was administered intravenously to the mice. The remaining antibodies in the blood stream were removed by perfusion and a single cell suspension was prepared. T cells in the bloodstream (circulating T cell) are labeled by antibodies, but T cells in lung tissue (lung-retentive T cells) are not labeled by antibodies. At 7 and 14 days after IL-7-mFc treatment, the numbers of cells labeled (in vivo $CD3^+$ in vitro $CD3^+$) or those not labeled (in vivo $CD3^-$ in vitro $CD3^+$) by in vivo CD3 label were analyzed. Through such method, it can be determined that the cells not labeled by in vivo CD3 label are lung retentive cells, and the cells labeled by in vivo CD3 label are those mainly in the bloodstream.

Figure 6:
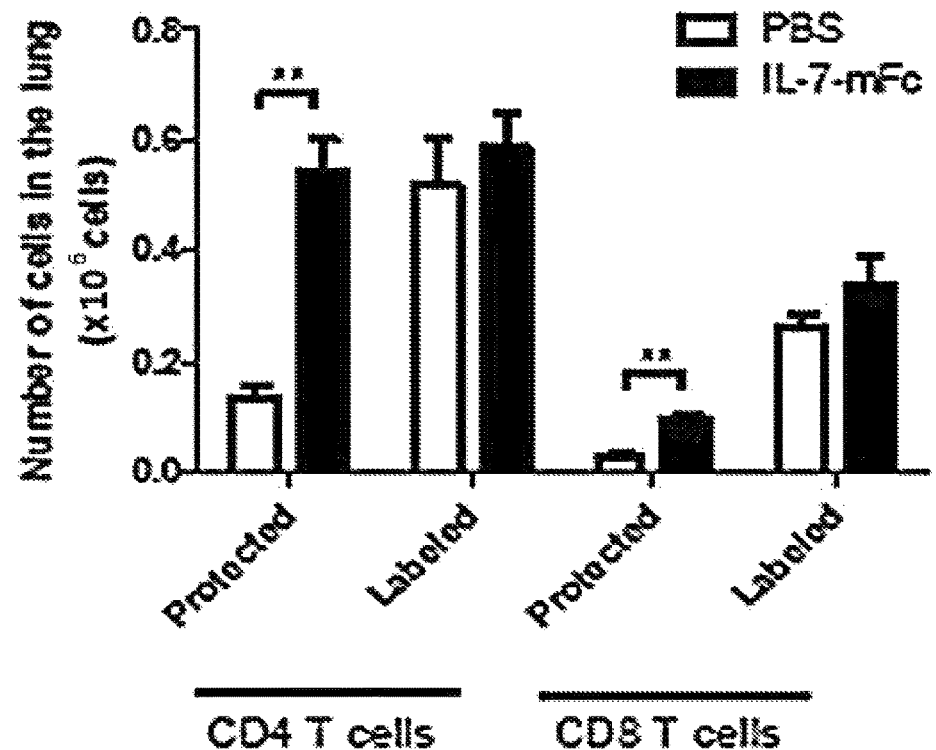
FIG. 6 is a graph showing analysis of $T_{RM}$-like T cells not exposed to the anti-CD3 antibody present in the blood stream but reside in the local tissues, by an in vivo labeling experiment for analyzing the histological location of pulmonary-derived T cells increased by IL-7-mFc treatment.

As shown in FIG. 6, the number of 'labeled' T cells returned to basal levels while the number of 'unlabelled' T cells was still significantly increased even at 14 days after treatment.

Example 8: Effect of Intranasal IL-7-Fc Fusion Protein Pretreatment on the Pulmonary T Cells and H5N2-Specific IgG Titer in the BALF after IAV Infection BALB/c mice were treated with IL-7-mFc intranasally and infected with 3 $LD_{50}$ of H5N2 after 14 days. Absolute numbers of T cells from total lung homogenate were measured at days 3 and 7 after infection. Frequency of $CD62L^{low}CD44^{high}$ population of CD8 and CD4 T cells were analyzed at day 7 after infection. Absolute number of pulmonary B and NK cells were measured at days 3 and 7 after infection. H5N2-specific IgG titer was analyzed in the BALF and sera at day 7 after infection. The results are shown in FIGS. 7a and 7b.

Figure 7A:
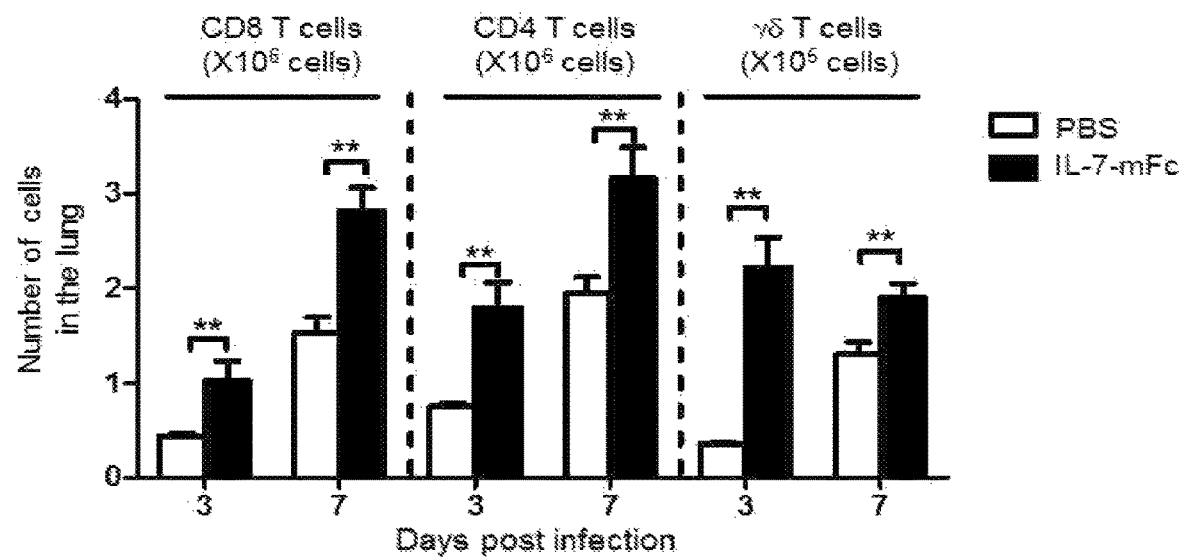
FIGS. 7a and 7b are graphs showing that activated T cells specifically increase and no change of antibody response is observed in the IL-7-mFc pre-administration group after the IAV infection.
Figure 7B:
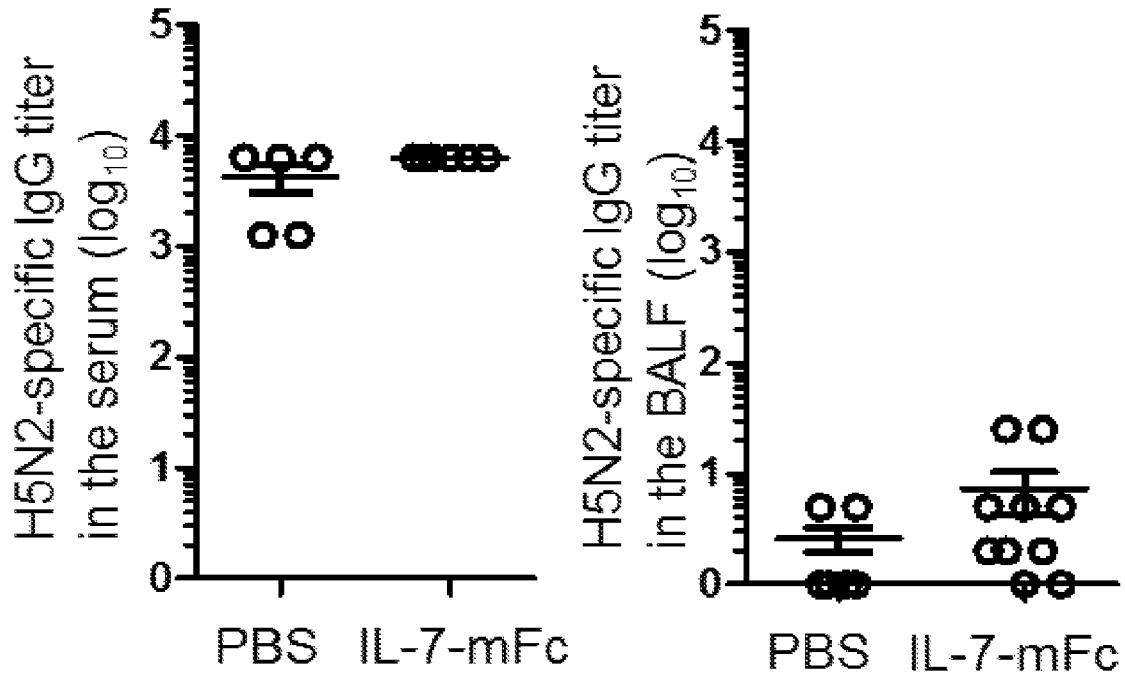

As shown in FIGS. 7a and 7b, the number of pulmonary T cells containing CD8, CD4 and γδ T cells was increased by IL-7-mFc pretreatment after IAV infection compared with PBS treatment, and IAV-specific IgG production in BALF and serum was not further up-regulated.

TABLE 1

| | Absolute cell numbers after IL-7-mFc treatment | | | | | |
|---|---|---|---|---|---|---|
| | Day 0 | Day 3 | Day 7 | Day 14 | Day 21 | Day 35 |
| Total CD4 T cells ($\times 10^6$) | 0.68 ± 0.07 | 0.76 ± 0.03 | 2.08 ± 0.28** | 0.89 ± 0.19 | 0.79 ± 0.14 | 0.70 ± 0.07 |
| $CD62L^{low}CD44^{high}$ CD4 T cells ($\times 10^5$) | 0.58 ± 0.08 | 1.44 ± 0.08** | 7.80 ± 1.24** | 1.61 ± 0.25** | 0.93 ± 0.05** | 0.69 ± 0.05 |
| Total CD8 T cells ($\times 10^6$) | 0.31 ± 0.07 | 0.32 ± 0.01 | 0.75 ± 0.11** | 0.42 ± 0.08 | 0.36 ± 0.08 | 0.28 ± 0.03 |
| $CD62L^{low}CD44^{high}$ CD8 T cells ($\times 10^5$) | 0.18 ± 0.03 | 0.29 ± 0.02* | 1.22 ± 0.14** | 0.50 ± 0.12* | 0.25 ± 0.03 | 0.26 ± 0.04 |
| γδ T cells ($\times 10^5$) | 0.24 ± 0.02 | 0.39 ± 0.01** | 4.71 ± 0.59** | 0.54 ± 0.16** | 0.40 ± 0.06* | 0.38 ± 0.02** |
| B cells ($\times 10^6$) | 0.84 ± 0.17 | 0.97 ± 0.03 | 2.27 ± 0.38* | 1.13 ± 0.10 | 0.83 ± 0.18 | N.D. |
| NK cells ($\times 10^6$) | 0.36 ± 0.03 | 0.58 ± 0.03* | 0.71 ± 0.07** | 0.39 ± 0.04 | 0.29 ± 0.05 | N.D. |

As shown in Table 1, IL-7-mFc significantly and temporarily increased the number of various immune cells including CD127 (receptor of IL-7)-expressing immune cells including CD4, CD8, γδ T cells and B cells.

These results indicate that the IL-7-Fc fusion protein induces a protective effect against fatal IAV infection by significantly increasing T cells directly involved in the immune response rather than the antibody response.

Example 9: Confirmation of the Relationship Between IL-7-Primed T Cells and Virus Removal The viral titer and relative expression of H5N2 NS-1 mRNA (normalized by housekeeping-gene L32) in total lung homogenate were analyzed at day 3 and 7 after infection. The results are shown in FIG. 8.

Figure 8:
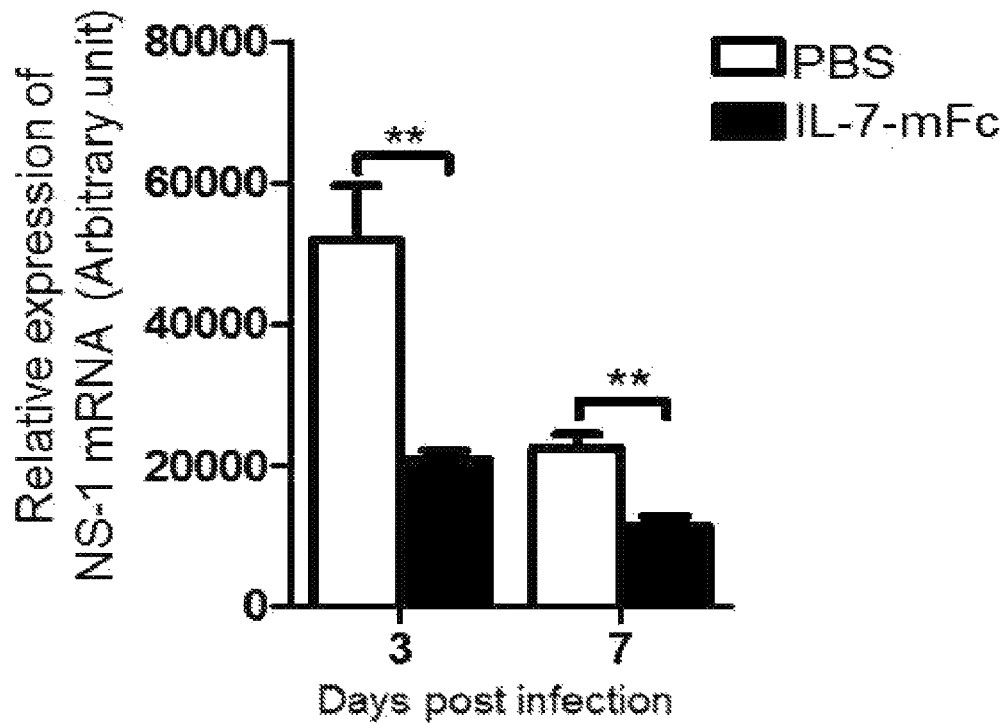
FIG. 8 is a graph showing the reduction of viral genes present in lung tissue of the IL-7-mFc pre-administration group after the IAV infection.

As shown in FIG. 8, the expression level of H5N2 NS-1 mRNA was greatly reduced in the total lung homogenate of IL-7-mFc-treated mice.

Example 10: Effect of IL-7-Fc Fusion Protein on Pulmonary Pathology Induced by IAV Infection BALB/c mice were treated with intranasal administration of IL-7-mFc, and after 14 days, infected with 3 $LD_{50}$ of H5N2. H & E staining and total inflammation index of lung sections at 50× magnification, and total protein concentration in BALF were analyzed at day 7 after infection.

Figure 9A:
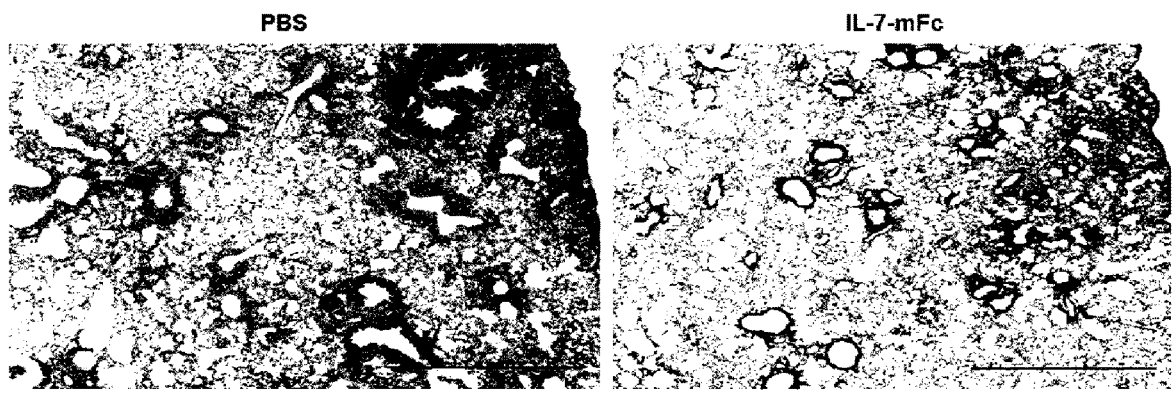
FIGS. 9a and 9b are graphs showing lung tissue lesions and the reducing effect of inflammatory cells in the IL-7-mFc pre-administration group after the IAV infection.
Figure 9B:
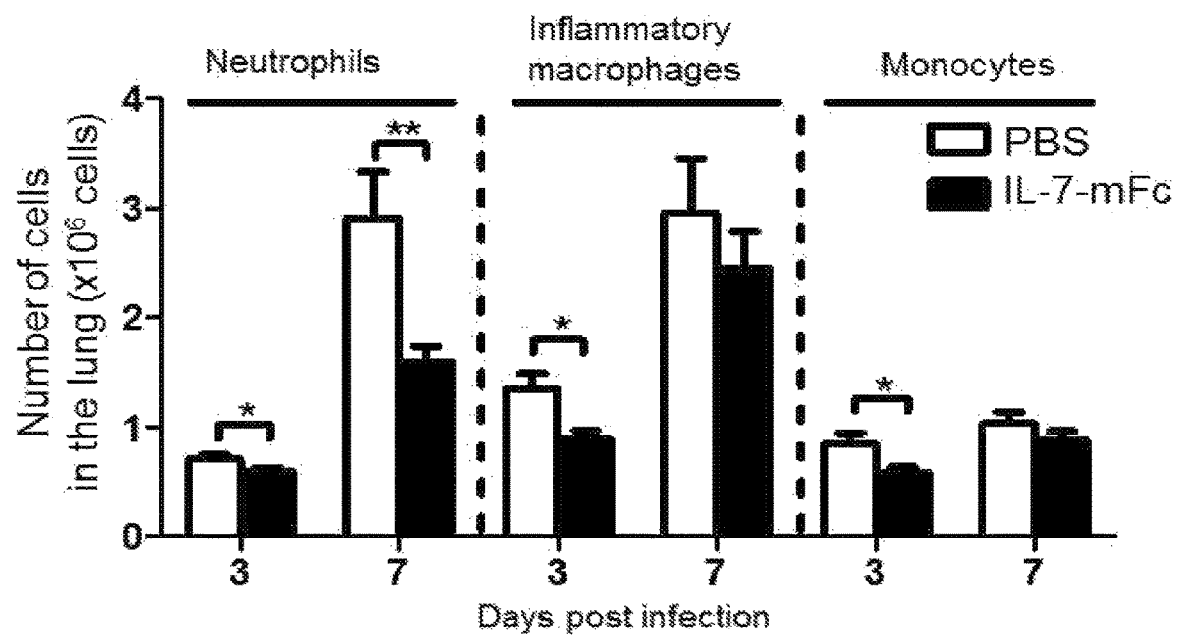

As shown in FIGS. 9a and 9b, the histopathological parameters for

Met Phe His Val Ser Phe Arg Tyr Ile Phe Gly Ile Pro Pro Leu Ile
1               5                   10                  15

Leu Val Leu Leu Pro Val Thr Ser Ser Asp Cys His Ile Lys Asp Lys
                20                  25                  30

Asp Gly Lys Ala Phe Gly Ser Val Leu Met Ile Ser Ile Asn Gln Leu
            35                  40                  45

Asp Lys Met Thr Gly Thr Asp Ser Asp Cys Pro Asn Asn Glu Pro Asn
        50                  55                  60

Phe Phe Lys Lys His Leu Cys Asp Asp Thr Lys Glu Ala Ala Phe Leu
65                  70                  75                  80

Asn Arg Ala Ala Arg Lys Leu Arg Gln Phe Leu Lys Met Asn Ile Ser
                85                  90                  95

Glu Glu Phe Asn Asp His Leu Leu Arg Val Ser Asp Gly Thr Gln Thr
                100                 105                 110

Leu Val Asn Cys Thr Ser Lys Glu Glu Lys Thr Ile Lys Glu Gln Lys
                115                 120                 125

Lys Asn Asp Pro Cys Phe Leu Lys Arg Leu Leu Arg Glu Ile Lys Thr
            130                 135                 140

Cys Trp Asn Lys Ile Leu Lys Gly Ser Ile
145                 150

<210> SEQ ID NO 3
<211> LENGTH: 154
<212> TYPE: PRT
<213> ORGANISM: Artificial Sequence
<220> FEATURE:
<223> OTHER INFORMATION: amino acid sequence of mouse IL-7 (Accession
      number : P10168)

<400> SEQUENCE: 3

Met Phe His Val Ser Phe Arg Tyr Ile Phe Gly Ile Pro Pro Leu Ile
1               5                   10                  15

Leu Val Leu Leu Pro Val Thr Ser Ser Glu Cys His Ile Lys Asp Lys
                20                  25                  30

Glu Gly Lys Ala Tyr Glu Ser Val Leu Met Ile Ser Ile Asp Glu Leu
            35                  40                  45

Asp Lys Met Thr Gly Thr Asp Ser Asn Cys Pro Asn Asn Glu Pro Asn
        50                  55                  60

Phe Phe Arg Lys His Val Cys Asp Asp Thr Lys Glu Ala Ala Phe Leu
65                  70                  75                  80

Asn Arg Ala Ala Arg Lys Leu Lys Gln Phe Leu Lys Met Asn Ile Ser
                85                  90                  95

Glu Glu Phe Asn Val His Leu Leu Thr Val Ser Gln Gly Thr Gln Thr
                100                 105                 110

Leu Val Asn Cys Thr Ser Lys Glu Glu Lys Asn Val Lys Glu Gln Lys
                115                 120                 125

Lys Asn Asp Ala Cys Phe Leu Lys Arg Leu Leu Arg Glu Ile Lys Thr
            130                 135                 140

Cys Trp Asn Lys Ile Leu Lys Gly Ser Ile
145                 150

<210> SEQ ID NO 4
<211> LENGTH: 177
<212> TYPE: PRT
<213> ORGANISM: Artificial Sequence
<220> FEATURE:
<223> OTHER INFORMATION: amino acid sequence of monkey IL-7 (Accession
      number : NP_001279008)

<400> SEQUENCE: 4

```
Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
                20                  25                  30

Asp Gly Lys Gln Tyr Glu Ser Val Leu Met Val Ser Ile Asp Gln Leu
            35                  40                  45

Leu Asp Ser Met Lys Glu Ile Gly Ser Asn Cys Leu Asn Asn Glu Phe
50                  55                  60

Asn Phe Phe Lys Arg His Leu Cys Asp Asp Asn Lys Glu Gly Met Phe
65                  70                  75                  80

Leu Phe Arg Ala Ala Arg Lys Leu Lys Gln Phe Leu Lys Met Asn Ser
                85                  90                  95

Thr Gly Asp Phe Asp Leu His Leu Leu Lys Val Ser Glu Gly Thr Thr
                100                 105                 110

Ile Leu Leu Asn Cys Thr Gly Lys Val Lys Gly Arg Lys Pro Ala Ala
            115                 120                 125

Leu Gly Glu Pro Gln Pro Thr Lys Ser Leu Glu Glu Asn Lys Ser Leu
130                 135                 140

Lys Glu Gln Lys Lys Leu Asn Asp Ser Cys Phe Leu Lys Arg Leu Leu
145                 150                 155                 160

Gln Lys Ile Lys Thr Cys Trp Asn Lys Ile Leu Met Gly Thr Lys Glu
                165                 170                 175

His
```

<210> SEQ ID NO 5
<211> LENGTH: 176
<212> TYPE: PRT
<213> ORGANISM: Artificial Sequence
<220> FEATURE:
<223> OTHER INFORMATION: amino acid sequence of cow IL-7 (Accession number : P26895)

<400> SEQUENCE: 5

```
Met Phe His Val Ser Phe Arg Tyr Ile Phe Gly Ile Pro Pro Leu Ile
1               5                   10                  15

Leu Val Leu Leu Pro Val Ala Ser Ser Asp Cys Asp Ile Ser Gly Lys
                20                  25                  30

Asp Gly Gly Ala Tyr Gln Asn Val Leu Met Val Asn Ile Asp Asp Leu
            35                  40                  45

Asp Asn Met Ile Asn Phe Asp Ser Asn Cys Leu Asn Asn Glu Pro Asn
50                  55                  60

Phe Phe Lys Lys His Ser Cys Asp Asp Asn Lys Glu Ala Ser Phe Leu
65                  70                  75                  80

Asn Arg Ala Ser Arg Lys Leu Arg Gln Phe Leu Lys Met Asn Ile Ser
                85                  90                  95

Asp Asp Phe Lys Leu His Leu Ser Thr Val Ser Gln Gly Thr Leu Thr
                100                 105                 110

Leu Leu Asn Cys Thr Ser Lys Gly Lys Gly Arg Lys Pro Pro Ser Leu
            115                 120                 125

Ser Glu Ala Gln Pro Thr Lys Asn Leu Glu Glu Asn Lys Ser Ser Lys
130                 135                 140

Glu Gln Lys Lys Gln Asn Asp Leu Cys Phe Leu Lys Ile Leu Leu Gln
145                 150                 155                 160
```

```
Lys Ile Lys Thr Cys Trp Asn Lys Ile Leu Arg Gly Ile Lys Glu His
                165                 170                 175

<210> SEQ ID NO 6
<211> LENGTH: 176
<212> TYPE: PRT
<213> ORGANISM: Artificial Sequence
<220> FEATURE:
<223> OTHER INFORMATION: amino acid sequence of sheep IL-7 (Accession
      number : Q28540)

<400> SEQUENCE: 6

Met Phe His Val Ser Phe Arg Tyr Ile Phe Gly Ile Pro Pro Leu Ile
1               5                   10                  15

Leu Val Leu Leu Pro Val Ala Ser Ser Asp Cys Asp Phe Ser Gly Lys
                20                  25                  30

Asp Gly Gly Ala Tyr Gln Asn Val Leu Met Val Ser Ile Asp Asp Leu
            35                  40                  45

Asp Asn Met Ile Asn Phe Asp Ser Asn Cys Leu Asn Asn Glu Pro Asn
        50                  55                  60

Phe Phe Lys Lys His Ser Cys Asp Asp Asn Lys Glu Ala Ser Phe Leu
65                  70                  75                  80

Asn Arg Ala Ala Arg Lys Leu Lys Gln Phe Leu Lys Met Asn Ile Ser
                85                  90                  95

Asp Asp Phe Lys Leu His Leu Ser Thr Val Ser Gln Gly Thr Leu Thr
            100                 105                 110

Leu Leu Asn Cys Thr Ser Lys Gly Lys Gly Arg Lys Pro Pro Ser Leu
        115                 120                 125

Gly Glu Ala Gln Pro Thr Lys Asn Leu Glu Glu Asn Lys Ser Leu Lys
130                 135                 140

Glu Gln Arg Lys Gln Asn Asp Leu Cys Phe Leu Lys Ile Leu Leu Gln
145                 150                 155                 160

Lys Ile Lys Thr Cys Trp Asn Lys Ile Leu Arg Gly Ile Thr Glu His
                165                 170                 175

<210> SEQ ID NO 7
<211> LENGTH: 384
<212> TYPE: PRT
<213> ORGANISM: Artificial Sequence
<220> FEATURE:
<223> OTHER INFORMATION: amino acid sequence of human IgD constant
      region (Genbank accession No. P01880)

<400> SEQUENCE: 7

Ala Pro Thr Lys Ala Pro Asp Val Phe Pro Ile Ile Ser Gly Cys Arg
1               5                   10                  15

His Pro Lys Asp Asn Ser Pro Val Val Leu Ala Cys Leu Ile Thr Gly
                20                  25                  30

Tyr His Pro Thr Ser Val Thr Val Thr Trp Tyr Met Gly Thr Gln Ser
            35                  40                  45

Gln Pro Gln Arg Thr Phe Pro Glu Ile Gln Arg Arg Asp Ser Tyr Tyr
        50                  55                  60

Met Thr Ser Ser Gln Leu Ser Thr Pro Leu Gln Gln Trp Arg Gln Gly
65                  70                  75                  80

Glu Tyr Lys Cys Val Val Gln His Thr Ala Ser Lys Ser Lys Lys Glu
                85                  90                  95

Ile Phe Arg Trp Pro Glu Ser Pro Lys Ala Gln Ala Ser Ser Val Pro
            100                 105                 110
```

```
Thr Ala Gln Pro Gln Ala Glu Gly Ser Leu Ala Lys Ala Thr Thr Ala
            115                 120                 125
Pro Ala Thr Thr Arg Asn Thr Gly Arg Gly Gly Glu Glu Lys Lys Lys
    130                 135                 140
Glu Lys Glu Lys Glu Glu Gln Glu Glu Arg Glu Thr Lys Thr Pro Glu
145                 150                 155                 160
Cys Pro Ser His Thr Gln Pro Leu Gly Val Tyr Leu Leu Thr Pro Ala
                165                 170                 175
Val Gln Asp Leu Trp Leu Arg Asp Lys Ala Thr Phe Thr Cys Phe Val
            180                 185                 190
Val Gly Ser Asp Leu Lys Asp Ala His Leu Thr Trp Glu Val Ala Gly
        195                 200                 205
Lys Val Pro Thr Gly Gly Val Glu Glu Gly Leu Leu Glu Arg His Ser
    210                 215                 220
Asn Gly Ser Gln Ser Gln His Ser Arg Leu Thr Leu Pro Arg Ser Leu
225                 230                 235                 240
Trp Asn Ala Gly Thr Ser Val Thr Cys Thr Leu Asn His Pro Ser Leu
                245                 250                 255
Pro Pro Gln Arg Leu Met Ala Leu Arg Glu Pro Ala Ala Gln Ala Pro
            260                 265                 270
Val Lys Leu Ser Leu Asn Leu Leu Ala Ser Ser Asp Pro Pro Glu Ala
        275                 280                 285
Ala Ser Trp Leu Leu Cys Glu Val Ser Gly Phe Ser Pro Pro Asn Ile
    290                 295                 300
Leu Leu Met Trp Leu Glu Asp Gln Arg Glu Val Asn Thr Ser Gly Phe
305                 310                 315                 320
Ala Pro Ala Arg Pro Pro Gln Pro Gly Ser Thr Thr Phe Trp Ala
                325                 330                 335
Trp Ser Val Leu Arg Val Pro Ala Pro Ser Pro Gln Pro Ala Thr
            340                 345                 350
Tyr Thr Cys Val Val Ser His Glu Asp Ser Arg Thr Leu Leu Asn Ala
        355                 360                 365
Ser Arg Ser Leu Glu Val Ser Tyr Val Thr Asp His Gly Pro Met Lys
    370                 375                 380

<210> SEQ ID NO 8
<211> LENGTH: 327
<212> TYPE: PRT
<213> ORGANISM: Artificial Sequence
<220> FEATURE:
<223> OTHER INFORMATION: amino acid sequence of Partial human IgG4
      constant region (Genbank accession No. AAH25985)

<400> SEQUENCE: 8

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
```

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 9
<211> LENGTH: 245
<212> TYPE: PRT
<213> ORGANISM: Artificial Sequence
<220> FEATURE:
<223> OTHER INFORMATION: amino acid sequence of hFc01

<400> SEQUENCE: 9

Arg Asn Thr Gly Arg Gly Gly Glu Glu Lys Lys Lys Glu Lys Glu Lys
1               5                   10                  15

Glu Glu Gln Glu Glu Arg Glu Thr Lys Thr Pro Glu Cys Pro Ser His
            20                  25                  30

Thr Gln Pro Leu Gly Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser Gln Glu Asp Pro Glu Val Gln Phe Asn Trp Tyr Val Asp Gly Val
65                  70                  75                  80

Glu Val His Asn Ala Lys Thr Lys Pro Arg Glu Glu Gln Phe Asn Ser
                85                  90                  95

Thr Tyr Arg Val Val Ser Val Leu Thr Val Leu His Gln Asp Trp Leu
            100                 105                 110

Asn Gly Lys Glu Tyr Lys Cys Lys Val Ser Asn Lys Gly Leu Pro Ser
        115                 120                 125

Ser Ile Glu Lys Thr Ile Ser Lys Ala Lys Gly Gln Pro Arg Glu Pro
130                 135                 140

Gln Val Tyr Thr Leu Pro Pro Ser Gln Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Arg Leu
        195                 200                 205

Thr Val Asp Lys Ser Arg Trp Gln Glu Gly Asn Val Phe Ser Cys Ser
210                 215                 220

Val Met His Glu Ala Leu His Asn His Tyr Thr Gln Lys Ser Leu Ser
225                 230                 235                 240

Leu Ser Leu Gly Lys
                245

<210> SEQ ID NO 10
<211> LENGTH: 245
<212> TYPE: PRT
<213> ORGANISM: Artificial Sequence
<220> FEATURE:
<223> OTHER INFORMATION: amino acid sequence of hFc02

<400> SEQUENCE: 10

Arg Asn Thr Gly Arg Gly Gly Glu Glu Lys Lys Gly Gly Lys Glu Lys
1               5                   10                  15

Glu Glu Gln Glu Glu Arg Glu Thr Lys Thr Pro Glu Cys Pro Ser His
            20                  25                  30

Thr Gln Pro Leu Gly Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser Gln Glu Asp Pro Glu Val Gln Phe Asn Trp Tyr Val Asp Gly Val
65                  70                  75                  80

Glu Val His Asn Ala Lys Thr Lys Pro Arg Glu Glu Gln Phe Asn Ser
                85                  90                  95

Thr Tyr Arg Val Val Ser Val Leu Thr Val Leu His Gln Asp Trp Leu
            100                 105                 110

Asn Gly Lys Glu Tyr Lys Cys Lys Val Ser Asn Lys Gly Leu Pro Ser
        115                 120                 125

Ser Ile Glu Lys Thr Ile Ser Lys Ala Lys Gly Gln Pro Arg Glu Pro
130                 135                 140

Gln Val Tyr Thr Leu Pro Pro Ser Gln Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Arg Leu
        195                 200                 205

Thr Val Asp Lys Ser Arg Trp Gln Glu Gly Asn Val Phe Ser Cys Ser
210                 215                 220

Val Met His Glu Ala Leu His Asn His Tyr Thr Gln Lys Ser Leu Ser
225                 230                 235                 240

Leu Ser Leu Gly Lys
            245

<210> SEQ ID NO 11
<211> LENGTH: 245
<212> TYPE: PRT
<213> ORGANISM: Artificial Sequence
<220> FEATURE:
<223> OTHER INFORMATION: amino acid sequence of hFc03

<400> SEQUENCE: 11

Arg Asn Thr Gly Arg Gly Gly Glu Glu Lys Lys Gly Ser Lys Glu Lys
1               5                   10                  15

Glu Glu Gln Glu Glu Arg Glu Thr Lys Thr Pro Glu Cys Pro Ser His
            20                  25                  30

Thr Gln Pro Leu Gly Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser Gln Glu Asp Pro Glu Val Gln Phe Asn Trp Tyr Val Asp Gly Val
65                  70                  75                  80

Glu Val His Asn Ala Lys Thr Lys Pro Arg Glu Glu Gln Phe Asn Ser
                85                  90                  95

Thr Tyr Arg Val Val Ser Val Leu Thr Val Leu His Gln Asp Trp Leu
            100                 105                 110

Asn Gly Lys Glu Tyr Lys Cys Lys Val Ser Asn Lys Gly Leu Pro Ser
        115                 120                 125

Ser Ile Glu Lys Thr Ile Ser Lys Ala Lys Gly Gln Pro Arg Glu Pro
    130                 135                 140

Gln Val Tyr Thr Leu Pro Pro Ser Gln Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Arg Leu
        195                 200                 205

Thr Val Asp Lys Ser Arg Trp Gln Glu Gly Asn Val Phe Ser Cys Ser
    210                 215                 220

Val Met His Glu Ala Leu His Asn His Tyr Thr Gln Lys Ser Leu Ser
225                 230                 235                 240

Leu Ser Leu Gly Lys
            245

<210> SEQ ID NO 12
<211> LENGTH: 245
<212> TYPE: PRT
<213> ORGANISM: Artificial Sequence
<220> FEATURE:
<223> OTHER INFORMATION: amino acid sequence of hFc04

<400> SEQUENCE: 12

Arg Asn Thr Gly Arg Gly Gly Glu Glu Lys Lys Ser Gly Lys Glu Lys
1               5                   10                  15

Glu Glu Gln Glu Glu Arg Glu Thr Lys Thr Pro Glu Cys Pro Ser His
            20                  25                  30

Thr Gln Pro Leu Gly Val Phe Leu Phe Pro Pro Lys Pro Lys Asp Thr

```
            35                  40                  45
Leu Met Ile Ser Arg Thr Pro Glu Val Thr Cys Val Val Asp Val
 50                  55                  60

Ser Gln Glu Asp Pro Glu Val Gln Phe Asn Trp Tyr Val Asp Gly Val
65                   70                  75                  80

Glu Val His Asn Ala Lys Thr Lys Pro Arg Glu Glu Gln Phe Asn Ser
                 85                  90                  95

Thr Tyr Arg Val Val Ser Val Leu Thr Val Leu His Gln Asp Trp Leu
            100                 105                 110

Asn Gly Lys Glu Tyr Lys Cys Lys Val Ser Asn Lys Gly Leu Pro Ser
        115                 120                 125

Ser Ile Glu Lys Thr Ile Ser Lys Ala Lys Gly Gln Pro Arg Glu Pro
    130                 135                 140

Gln Val Tyr Thr Leu Pro Pro Ser Gln Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Arg Leu
        195                 200                 205

Thr Val Asp Lys Ser Arg Trp Gln Glu Gly Asn Val Phe Ser Cys Ser
    210                 215                 220

Val Met His Glu Ala Leu His Asn His Tyr Thr Gln Lys Ser Leu Ser
225                 230                 235                 240

Leu Ser Leu Gly Lys
            245

<210> SEQ ID NO 13
<211> LENGTH: 245
<212> TYPE: PRT
<213> ORGANISM: Artificial Sequence
<220> FEATURE:
<223> OTHER INFORMATION: amino acid sequence of hFc05

<400> SEQUENCE: 13

Arg Asn Thr Gly Arg Gly Gly Glu Glu Lys Lys Ser Lys Glu Lys
1               5                   10                  15

Glu Glu Gln Glu Glu Arg Glu Thr Lys Thr Pro Glu Cys Pro Ser His
            20                  25                  30

Thr Gln Pro Leu Gly Val Phe Leu Phe Pro Pro Lys Pro Lys Asp Thr
        35                  40                  45

Leu Met Ile Ser Arg Thr Pro Glu Val Thr Cys Val Val Asp Val
 50                  55                  60

Ser Gln Glu Asp Pro Glu Val Gln Phe Asn Trp Tyr Val Asp Gly Val
65                   70                  75                  80

Glu Val His Asn Ala Lys Thr Lys Pro Arg Glu Glu Gln Phe Asn Ser
                 85                  90                  95

Thr Tyr Arg Val Val Ser Val Leu Thr Val Leu His Gln Asp Trp Leu
            100                 105                 110

Asn Gly Lys Glu Tyr Lys Cys Lys Val Ser Asn Lys Gly Leu Pro Ser
        115                 120                 125

Ser Ile Glu Lys Thr Ile Ser Lys Ala Lys Gly Gln Pro Arg Glu Pro
    130                 135                 140

Gln Val Tyr Thr Leu Pro Pro Ser Gln Glu Glu Met Thr Lys Asn Gln
```

```
            145                 150                 155                 160
        Val Ser Leu Thr Cys Leu Val Lys Gly Phe Tyr Pro Ser Asp Ile Ala
                        165                 170                 175

Val Glu Trp Glu Ser Asn Gly Gln Pro Glu Asn Asn Tyr Lys Thr Thr
                        180                 185                 190

Pro Pro Val Leu Asp Ser Asp Gly Ser Phe Phe Leu Tyr Ser Arg Leu
                        195                 200                 205

Thr Val Asp Lys Ser Arg Trp Gln Gln Gly Asn Val Phe Ser Cys Ser
                        210                 215                 220

Val Met His Glu Ala Leu His Asn His Tyr Thr Gln Lys Ser Leu Ser
        225                 230                 235                 240

Leu Ser Leu Gly Lys
                        245

<210> SEQ ID NO 14
<211> LENGTH: 243
<212> TYPE: PRT
<213> ORGANISM: Artificial Sequence
<220> FEATURE:
<223> OTHER INFORMATION: amino acid sequence of mouse IgG Fc variant

<400> SEQUENCE: 14

Ala Ser Ala Glu Pro Arg Gly Pro Thr Ile Lys Pro Cys Pro Pro Cys
        1               5                   10                  15

Lys Cys Pro Ala Pro Asn Leu Glu Gly Gly Pro Ser Val Phe Ile Phe
                        20                  25                  30

Pro Pro Lys Ile Lys Asp Val Leu Met Ile Ser Leu Ser Pro Ile Val
                        35                  40                  45

Thr Cys Val Val Val Asp Val Ser Glu Asp Asp Pro Asp Val Gln Ile
                50                  55                  60

Ser Trp Phe Val Asn Asn Val Glu Val His Thr Ala Gln Thr Gln Thr
        65                  70                  75                  80

His Arg Glu Asp Tyr Asn Ser Thr Leu Arg Val Val Ser Ala Leu Pro
                        85                  90                  95

Ile Gln His Gln Asp Trp Met Ser Gly Lys Ala Phe Ala Cys Ala Val
                        100                 105                 110

Asn Asn Lys Asp Leu Pro Ala Pro Ile Glu Arg Thr Ile Ser Lys Pro
                        115                 120                 125

Lys Gly Ser Val Arg Ala Pro Gln Val Tyr Val Leu Pro Pro Pro Glu
                        130                 135                 140

Glu Glu Met Thr Lys Lys Gln Val Thr Leu Thr Cys Met Val Thr Asp
        145                 150                 155                 160

Phe Met Pro Glu Asp Ile Tyr Val Glu Trp Thr Asn Asn Gly Lys Thr
                        165                 170                 175

Glu Leu Asn Tyr Lys Asn Thr Glu Pro Val Leu Asp Ser Asp Gly Ser
                        180                 185                 190

Tyr Phe Met Tyr Ser Lys Leu Arg Val Glu Lys Lys Asn Trp Val Glu
                        195                 200                 205

Arg Asn Ser Tyr Ser Cys Ser Val Val His Glu Gly Leu His Asn His
                        210                 215                 220

His Thr Thr Lys Ser Phe Ser Arg Thr Pro Gly Lys Gly Gly Gly Asn
        225                 230                 235                 240

Ser Gly Ser

<210> SEQ ID NO 15
```

```
<211> LENGTH: 153
<212> TYPE: PRT
<213> ORGANISM: Artificial Sequence
<220> FEATURE:
<223> OTHER INFORMATION: amino acid sequence of modified IL-7(M)

<400> SEQUENCE: 15

Met Asp Cys Asp Ile Glu Gly Lys Asp Gly Lys Gln Tyr Glu Ser Val
1               5                   10                  15

Leu Met Val Ser Ile Asp Gln Leu Leu Asp Ser Met Lys Glu Ile Gly
            20                  25                  30

Ser Asn Cys Leu Asn Asn Glu Phe Asn Phe Phe Lys Arg His Ile Cys
        35                  40                  45

Asp Ala Asn Lys Glu Gly Met Phe Leu Phe Arg Ala Ala Arg Lys Leu
    50                  55                  60

Arg Gln Phe Leu Lys Met Asn Ser Thr Gly Asp Phe Asp Leu His Leu
65                  70                  75                  80

Leu Lys Val Ser Glu Gly Thr Thr Ile Leu Leu Asn Cys Thr Gly Gln
                85                  90                  95

Val Lys Gly Arg Lys Pro Ala Ala Leu Gly Glu Ala Gln Pro Thr Lys
            100                 105                 110

Ser Leu Glu Glu Asn Lys Ser Leu Lys Glu Gln Lys Lys Leu Asn Asp
        115                 120                 125

Leu Cys Phe Leu Lys Arg Leu Leu Gln Glu Ile Lys Thr Cys Trp Asn
    130                 135                 140

Lys Ile Leu Met Gly Thr Lys Glu His
145                 150

<210> SEQ ID NO 16
<211> LENGTH: 154
<212> TYPE: PRT
<213> ORGANISM: Artificial Sequence
<220> FEATURE:
<223> OTHER INFORMATION: amino acid sequence of modified IL-7(MM)

<400> SEQUENCE: 16

Met Met Asp Cys Asp Ile Glu Gly Lys Asp Gly Lys Gln Tyr Glu Ser
1               5                   10                  15

Val Leu Met Val Ser Ile Asp Gln Leu Leu Asp Ser Met Lys Glu Ile
            20                  25                  30

Gly Ser Asn Cys Leu Asn Asn Glu Phe Asn Phe Phe Lys Arg His Ile
        35                  40                  45

Cys Asp Ala Asn Lys Glu Gly Met Phe Leu Phe Arg Ala Ala Arg Lys
    50                  55                  60

Leu Arg Gln Phe Leu Lys Met Asn Ser Thr Gly Asp Phe Asp Leu His
65                  70                  75                  80

Leu Leu Lys Val Ser Glu Gly Thr Thr Ile Leu Leu Asn Cys Thr Gly
                85                  90                  95

Gln Val Lys Gly Arg Lys Pro Ala Ala Leu Gly Glu Ala Gln Pro Thr
            100                 105                 110

Lys Ser Leu Glu Glu Asn Lys Ser Leu Lys Glu Gln Lys Lys Leu Asn
        115                 120                 125

Asp Leu Cys Phe Leu Lys Arg Leu Leu Gln Glu Ile Lys Thr Cys Trp
    130                 135                 140

Asn Lys Ile Leu Met Gly Thr Lys Glu His
145                 150
```

```
<210> SEQ ID NO 17
<211> LENGTH: 155
<212> TYPE: PRT
<213> ORGANISM: Artificial Sequence
<220> FEATURE:
<223> OTHER INFORMATION: amino acid sequence of modified IL-7(MMM)

<400> SEQUENCE: 17

Met Met Met Asp Cys Asp Ile Glu Gly Lys Asp Gly Lys Gln Tyr Glu
1               5                   10                  15

Ser Val Leu Met Val Ser Ile Asp Gln Leu Leu Asp Ser Met Lys Glu
                20                  25                  30

Ile Gly Ser Asn Cys Leu Asn Asn Glu Phe Asn Phe Phe Lys Arg His
            35                  40                  45

Ile Cys Asp Ala Asn Lys Glu Gly Met Phe Leu Phe Arg Ala Ala Arg
        50                  55                  60

Lys Leu Arg Gln Phe Leu Lys Met Asn Ser Thr Gly Asp Phe Asp Leu
65                  70                  75                  80

His Leu Leu Lys Val Ser Glu Gly Thr Thr Ile Leu Leu Asn Cys Thr
                85                  90                  95

Gly Gln Val Lys Gly Arg Lys Pro Ala Ala Leu Gly Glu Ala Gln Pro
            100                 105                 110

Thr Lys Ser Leu Glu Glu Asn Lys Ser Leu Lys Glu Gln Lys Lys Leu
        115                 120                 125

Asn Asp Leu Cys Phe Leu Lys Arg Leu Leu Gln Glu Ile Lys Thr Cys
    130                 135                 140

Trp Asn Lys Ile Leu Met Gly Thr Lys Glu His
145                 150                 155

<210> SEQ ID NO 18
<211> LENGTH: 155
<212> TYPE: PRT
<213> ORGANISM: Artificial Sequence
<220> FEATURE:
<223> OTHER INFORMATION: amino acid sequence of modified IL-7(MGM)

<400> SEQUENCE: 18

Met Gly Met Asp Cys Asp Ile Glu Gly Lys Asp Gly Lys Gln Tyr Glu
1               5                   10                  15

Ser Val Leu Met Val Ser Ile Asp Gln Leu Leu Asp Ser Met Lys Glu
                20                  25                  30

Ile Gly Ser Asn Cys Leu Asn Asn Glu Phe Asn Phe Phe Lys Arg His
            35                  40                  45

Ile Cys Asp Ala Asn Lys Glu Gly Met Phe Leu Phe Arg Ala Ala Arg
        50                  55                  60

Lys Leu Arg Gln Phe Leu Lys Met Asn Ser Thr Gly Asp Phe Asp Leu
65                  70                  75                  80

His Leu Leu Lys Val Ser Glu Gly Thr Thr Ile Leu Leu Asn Cys Thr
                85                  90                  95

Gly Gln Val Lys Gly Arg Lys Pro Ala Ala Leu Gly Glu Ala Gln Pro
            100                 105                 110

Thr Lys Ser Leu Glu Glu Asn Lys Ser Leu Lys Glu Gln Lys Lys Leu
        115                 120                 125

Asn Asp Leu Cys Phe Leu Lys Arg Leu Leu Gln Glu Ile Lys Thr Cys
    130                 135                 140

Trp Asn Lys Ile Leu Met Gly Thr Lys Glu His
145                 150                 155
```

-continued

```
<210> SEQ ID NO 19
<211> LENGTH: 155
<212> TYPE: PRT
<213> ORGANISM: Artificial Sequence
<220> FEATURE:
<223> OTHER INFORMATION: amino acid sequence of modified IL-7(DDD)

<400> SEQUENCE: 19

Asp Asp Asp Asp Cys Asp Ile Glu Gly Lys Asp Gly Lys Gln Tyr Glu
1               5                   10                  15

Ser Val Leu Met Val Ser Ile Asp Gln Leu Leu Asp Ser Met Lys Glu
            20                  25                  30

Ile Gly Ser Asn Cys Leu Asn Asn Glu Phe Asn Phe Lys Arg His
        35                  40                  45

Ile Cys Asp Ala Asn Lys Glu Gly Met Phe Leu Phe Arg Ala Ala Arg
 50                  55                  60

Lys Leu Arg Gln Phe Leu Lys Met Asn Ser Thr Gly Asp Phe Asp Leu
 65                  70                  75                  80

His Leu Leu Lys Val Ser Glu Gly Thr Thr Ile Leu Leu Asn Cys Thr
                85                  90                  95

Gly Gln Val Lys Gly Arg Lys Pro Ala Ala Leu Gly Glu Ala Gln Pro
            100                 105                 110

Thr Lys Ser Leu Glu Glu Asn Lys Ser Leu Lys Glu Gln Lys Lys Leu
        115                 120                 125

Asn Asp Leu Cys Phe Leu Lys Arg Leu Leu Gln Glu Ile Lys Thr Cys
    130                 135                 140

Trp Asn Lys Ile Leu Met Gly Thr Lys Glu His
145                 150                 155

<210> SEQ ID NO 20
<211> LENGTH: 156
<212> TYPE: PRT
<213> ORGANISM: Artificial Sequence
<220> FEATURE:
<223> OTHER INFORMATION: amino acid sequence of modified IL-7(MMMM)

<400> SEQUENCE: 20

Met Met Met Met Asp Cys Asp Ile Glu Gly Lys Asp Gly Lys Gln Tyr
1               5                   10                  15

Glu Ser Val Leu Met Val Ser Ile Asp Gln Leu Leu Asp Ser Met Lys
            20                  25                  30

Glu Ile Gly Ser Asn Cys Leu Asn Asn Glu Phe Asn Phe Lys Arg
        35                  40                  45

His Ile Cys Asp Ala Asn Lys Glu Gly Met Phe Leu Phe Arg Ala Ala
 50                  55                  60

Arg Lys Leu Arg Gln Phe Leu Lys Met Asn Ser Thr Gly Asp Phe Asp
 65                  70                  75                  80

Leu His Leu Leu Lys Val Ser Glu Gly Thr Thr Ile Leu Leu Asn Cys
                85                  90                  95

Thr Gly Gln Val Lys Gly Arg Lys Pro Ala Ala Leu Gly Glu Ala Gln
            100                 105                 110

Pro Thr Lys Ser Leu Glu Glu Asn Lys Ser Leu Lys Glu Gln Lys Lys
        115                 120                 125

Leu Asn Asp Leu Cys Phe Leu Lys Arg Leu Leu Gln Glu Ile Lys Thr
    130                 135                 140

Cys Trp Asn Lys Ile Leu Met Gly Thr Lys Glu His
145                 150                 155
```

<210> SEQ ID NO 21
<211> LENGTH: 398
<212> TYPE: PRT
<213> ORGANISM: Artificial Sequence
<220> FEATURE:
<223> OTHER INFORMATION: amino acid sequence of modified IL-7(M) fused hyFc

<400> SEQUENCE: 21

```
Met Asp Cys Asp Ile Glu Gly Lys Asp Gly Lys Gln Tyr Glu Ser Val
1               5                   10                  15

Leu Met Val Ser Ile Asp Gln Leu Leu Asp Ser Met Lys Glu Ile Gly
            20                  25                  30

Ser Asn Cys Leu Asn Asn Glu Phe Asn Phe Phe Lys Arg His Ile Cys
        35                  40                  45

Asp Ala Asn Lys Glu Gly Met Phe Leu Phe Arg Ala Ala Arg Lys Leu
    50                  55                  60

Arg Gln Phe Leu Lys Met Asn Ser Thr Gly Asp Phe Asp Leu His Leu
65                  70                  75                  80

Leu Lys Val Ser Glu Gly Thr Thr Ile Leu Leu Asn Cys Thr Gly Gln
                85                  90                  95

Val Lys Gly Arg Lys Pro Ala Ala Leu Gly Glu Ala Gln Pro Thr Lys
            100                 105                 110

Ser Leu Glu Glu Asn Lys Ser Leu Lys Glu Gln Lys Lys Leu Asn Asp
        115                 120                 125

Leu Cys Phe Leu Lys Arg Leu Leu Gln Glu Ile Lys Thr Cys Trp Asn
    130                 135                 140

Lys Ile Leu Met Gly Thr Lys Glu His Arg Asn Thr Gly Arg Gly Gly
145                 150                 155                 160

Glu Glu Lys Lys Lys Glu Lys Glu Glu Gln Glu Glu Arg Glu
                165                 170                 175

Thr Lys Thr Pro Glu Cys Pro Ser His Thr Gln Pro Leu Gly Val Phe
            180                 185                 190

Leu Phe Pro Pro Lys Pro Lys Asp Thr Leu Met Ile Ser Arg Thr Pro
        195                 200                 205

Glu Val Thr Cys Val Val Val Asp Val Ser Gln Glu Asp Pro Glu Val
    210                 215                 220

Gln Phe Asn Trp Tyr Val Asp Gly Val Glu Val His Asn Ala Lys Thr
225                 230                 235                 240

Lys Pro Arg Glu Glu Gln Phe Asn Ser Thr Tyr Arg Val Val Ser Val
                245                 250                 255

Leu Thr Val Leu His Gln Asp Trp Leu Asn Gly Lys Glu Tyr Lys Cys
            260                 265                 270

Lys Val Ser Asn Lys Gly Leu Pro Ser Ser Ile Glu Lys Thr Ile Ser
        275                 280                 285

Lys Ala Lys Gly Gln Pro Arg Glu Pro Gln Val Tyr Thr Leu Pro Pro
    290                 295                 300

Ser Gln Glu Glu Met Thr Lys Asn Gln Val Ser Leu Thr Cys Leu Val
305                 310                 315                 320

Lys Gly Phe Tyr Pro Ser Asp Ile Ala Val Glu Trp Glu Ser Asn Gly
                325                 330                 335

Gln Pro Glu Asn Asn Tyr Lys Thr Thr Pro Pro Val Leu Asp Ser Asp
            340                 345                 350

Gly Ser Phe Phe Leu Tyr Ser Arg Leu Thr Val Asp Lys Ser Arg Trp
```

```
                  355                 360                 365
Gln Glu Gly Asn Val Phe Ser Cys Ser Val Met His Glu Ala Leu His
         370                 375                 380

Asn His Tyr Thr Gln Lys Ser Leu Ser Leu Ser Leu Gly Lys
385                 390                 395

<210> SEQ ID NO 22
<211> LENGTH: 399
<212> TYPE: PRT
<213> ORGANISM: Artificial Sequence
<220> FEATURE:
<223> OTHER INFORMATION: amino acid sequence of modified IL-7(MM) fused
      hyFc

<400> SEQUENCE: 22

Met Met Asp Cys Asp Ile Glu Gly Lys Asp Gly Lys Gln Tyr Glu Ser
1               5                  10                  15

Val Leu Met Val Ser Ile Asp Gln Leu Leu Asp Ser Met Lys Glu Ile
            20                  25                  30

Gly Ser Asn Cys Leu Asn Asn Glu Phe Asn Phe Phe Lys Arg His Ile
        35                  40                  45

Cys Asp Ala Asn Lys Glu Gly Met Phe Leu Phe Arg Ala Ala Arg Lys
50                  55                  60

Leu Arg Gln Phe Leu Lys Met Asn Ser Thr Gly Asp Phe Asp Leu His
65                  70                  75                  80

Leu Leu Lys Val Ser Glu Gly Thr Thr Ile Leu Leu Asn Cys Thr Gly
                85                  90                  95

Gln Val Lys Gly Arg Lys Pro Ala Ala Leu Gly Glu Ala Gln Pro Thr
            100                 105                 110

Lys Ser Leu Glu Glu Asn Lys Ser Leu Lys Glu Gln Lys Lys Leu Asn
        115                 120                 125

Asp Leu Cys Phe Leu Lys Arg Leu Leu Gln Glu Ile Lys Thr Cys Trp
130                 135                 140

Asn Lys Ile Leu Met Gly Thr Lys Glu His Arg Asn Thr Gly Arg Gly
145                 150                 155                 160

Gly Glu Glu Lys Lys Lys Glu Lys Glu Glu Gln Glu Glu Arg
                165                 170                 175

Glu Thr Lys Thr Pro Glu Cys Pro Ser His Thr Gln Pro Leu Gly Val
            180                 185                 190

Phe Leu Phe Pro Pro Lys Pro Lys Asp Thr Leu Met Ile Ser Arg Thr
        195                 200                 205

Pro Glu Val Thr Cys Val Val Val Asp Val Ser Gln Glu Asp Pro Glu
210                 215                 220

Val Gln Phe Asn Trp Tyr Val Asp Gly Val Glu Val His Asn Ala Lys
225                 230                 235                 240

Thr Lys Pro Arg Glu Glu Gln Phe Asn Ser Thr Tyr Arg Val Val Ser
                245                 250                 255

Val Leu Thr Val Leu His Gln Asp Trp Leu Asn Gly Lys Glu Tyr Lys
            260                 265                 270

Cys Lys Val Ser Asn Lys Gly Leu Pro Ser Ser Ile Glu Lys Thr Ile
        275                 280                 285

Ser Lys Ala Lys Gly Gln Pro Arg Glu Pro Gln Val Tyr Thr Leu Pro
290                 295                 300

Pro Ser Gln Glu Glu Met Thr Lys Asn Gln Val Ser Leu Thr Cys Leu
305                 310                 315                 320
```

Val Lys Gly Phe Tyr Pro Ser Asp Ile Ala Val Glu Trp Glu Ser Asn
            325                 330                 335

Gly Gln Pro Glu Asn Asn Tyr Lys Thr Thr Pro Pro Val Leu Asp Ser
            340                 345                 350

Asp Gly Ser Phe Phe Leu Tyr Ser Arg Leu Thr Val Asp Lys Ser Arg
            355                 360                 365

Trp Gln Glu Gly Asn Val Phe Ser Cys Ser Val Met His Glu Ala Leu
            370                 375                 380

His Asn His Tyr Thr Gln Lys Ser Leu Ser Leu Ser Leu Gly Lys
385                 390                 395

<210> SEQ ID NO 23
<211> LENGTH: 400
<212> TYPE: PRT
<213> ORGANISM: Artificial Sequence
<220> FEATURE:
<223> OTHER INFORMATION: amino acid sequence of modified IL-7(MMM) fused
      hyFc

<400> SEQUENCE: 23

Met Met Met Asp Cys Asp Ile Glu Gly Lys Asp Gly Lys Gln Tyr Glu
1               5                   10                  15

Ser Val Leu Met Val Ser Ile Asp Gln Leu Leu Asp Ser Met Lys Glu
            20                  25                  30

Ile Gly Ser Asn Cys Leu Asn Asn Glu Phe Asn Phe Phe Lys Arg His
            35                  40                  45

Ile Cys Asp Ala Asn Lys Glu Gly Met Phe Leu Phe Arg Ala Ala Arg
        50                  55                  60

Lys Leu Arg Gln Phe Leu Lys Met Asn Ser Thr Gly Asp Phe Asp Leu
65                  70                  75                  80

His Leu Leu Lys Val Ser Glu Gly Thr Thr Ile Leu Leu Asn Cys Thr
                85                  90                  95

Gly Gln Val Lys Gly Arg Lys Pro Ala Ala Leu Gly Glu Ala Gln Pro
            100                 105                 110

Thr Lys Ser Leu Glu Glu Asn Lys Ser Leu Lys Glu Gln Lys Lys Leu
            115                 120                 125

Asn Asp Leu Cys Phe Leu Lys Arg Leu Leu Gln Glu Ile Lys Thr Cys
        130                 135                 140

Trp Asn Lys Ile Leu Met Gly Thr Lys Glu His Arg Asn Thr Gly Arg
145                 150                 155                 160

Gly Gly Glu Glu Lys Lys Lys Glu Lys Glu Lys Glu Gln Glu Glu
                165                 170                 175

Arg Glu Thr Lys Thr Pro Glu Cys Pro Ser His Thr Gln Pro Leu Gly
            180                 185                 190

Val Phe Leu Phe Pro Pro Lys Pro Lys Asp Thr Leu Met Ile Ser Arg
            195                 200                 205

Thr Pro Glu Val Thr Cys Val Val Val Asp Val Ser Gln Glu Asp Pro
        210                 215                 220

Glu Val Gln Phe Asn Trp Tyr Val Asp Gly Val Glu Val His Asn Ala
225                 230                 235                 240

Lys Thr Lys Pro Arg Glu Glu Gln Phe Asn Ser Thr Tyr Arg Val Val
                245                 250                 255

Ser Val Leu Thr Val Leu His Gln Asp Trp Leu Asn Gly Lys Glu Tyr
            260                 265                 270

Lys Cys Lys Val Ser Asn Lys Gly Leu Pro Ser Ser Ile Glu Lys Thr
            275                 280                 285

```
Ile Ser Lys Ala Lys Gly Gln Pro Arg Glu Pro Gln Val Tyr Thr Leu
290                 295                 300

Pro Pro Ser Gln Glu Glu Met Thr Lys Asn Gln Val Ser Leu Thr Cys
305                 310                 315                 320

Leu Val Lys Gly Phe Tyr Pro Ser Asp Ile Ala Val Glu Trp Glu Ser
                325                 330                 335

Asn Gly Gln Pro Glu Asn Asn Tyr Lys Thr Thr Pro Pro Val Leu Asp
                340                 345                 350

Ser Asp Gly Ser Phe Phe Leu Tyr Ser Arg Leu Thr Val Asp Lys Ser
                355                 360                 365

Arg Trp Gln Glu Gly Asn Val Phe Ser Cys Ser Val Met His Glu Ala
                370                 375                 380

Leu His Asn His Tyr Thr Gln Lys Ser Leu Ser Leu Ser Leu Gly Lys
385                 390                 395                 400

<210> SEQ ID NO 24
<211> LENGTH: 400
<212> TYPE: PRT
<213> ORGANISM: Artificial Sequence
<220> FEATURE:
<223> OTHER INFORMATION: amino acid sequence of modified IL-7(MGM) fused
      hyFc

<400> SEQUENCE: 24

Met Gly Met Asp Cys Asp Ile Glu Gly Lys Asp Gly Lys Gln Tyr Glu
1               5                   10                  15

Ser Val Leu Met Val Ser Ile Asp Gln Leu Leu Asp Ser Met Lys Glu
                20                  25                  30

Ile Gly Ser Asn Cys Leu Asn Asn Glu Phe Asn Phe Phe Lys Arg His
                35                  40                  45

Ile Cys Asp Ala Asn Lys Glu Gly Met Phe Leu Phe Arg Ala Ala Arg
            50                  55                  60

Lys Leu Arg Gln Phe Leu Lys Met Asn Ser Thr Gly Asp Phe Asp Leu
65                  70                  75                  80

His Leu Leu Lys Val Ser Glu Gly Thr Thr Ile Leu Leu Asn Cys Thr
                85                  90                  95

Gly Gln Val Lys Gly Arg Lys Pro Ala Ala Leu Gly Glu Ala Gln Pro
                100                 105                 110

Thr Lys Ser Leu Glu Glu Asn Lys Ser Leu Lys Glu Gln Lys Lys Leu
                115                 120                 125

Asn Asp Leu Cys Phe Leu Lys Arg Leu Leu Gln Glu Ile Lys Thr Cys
            130                 135                 140

Trp Asn Lys Ile Leu Met Gly Thr Lys Glu His Arg Asn Thr Gly Arg
145                 150                 155                 160

Gly Gly Glu Glu Lys Lys Lys Glu Lys Glu Lys Glu Gln Glu Glu
                165                 170                 175

Arg Glu Thr Lys Thr Pro Glu Cys Pro Ser His Thr Gln Pro Leu Gly
                180                 185                 190

Val Phe Leu Phe Pro Pro Lys Pro Lys Asp Thr Leu Met Ile Ser Arg
                195                 200                 205

Thr Pro Glu Val Thr Cys Val Val Val Asp Val Ser Gln Glu Asp Pro
            210                 215                 220

Glu Val Gln Phe Asn Trp Tyr Val Asp Gly Val Glu Val His Asn Ala
225                 230                 235                 240

Lys Thr Lys Pro Arg Glu Glu Gln Phe Asn Ser Thr Tyr Arg Val Val
```

```
                        245                 250                 255
Ser Val Leu Thr Val Leu His Gln Asp Trp Leu Asn Gly Lys Glu Tyr
                260                 265                 270

Lys Cys Lys Val Ser Asn Lys Gly Leu Pro Ser Ser Ile Glu Lys Thr
            275                 280                 285

Ile Ser Lys Ala Lys Gly Gln Pro Arg Glu Pro Gln Val Tyr Thr Leu
        290                 295                 300

Pro Pro Ser Gln Glu Glu Met Thr Lys Asn Gln Val Ser Leu Thr Cys
305                 310                 315                 320

Leu Val Lys Gly Phe Tyr Pro Ser Asp Ile Ala Val Glu Trp Glu Ser
                325                 330                 335

Asn Gly Gln Pro Glu Asn Asn Tyr Lys Thr Thr Pro Pro Val Leu Asp
            340                 345                 350

Ser Asp Gly Ser Phe Phe Leu Tyr Ser Arg Leu Thr Val Asp Lys Ser
        355                 360                 365

Arg Trp Gln Glu Gly Asn Val Phe Ser Cys Ser Val Met His Glu Ala
    370                 375                 380

Leu His Asn His Tyr Thr Gln Lys Ser Leu Ser Leu Ser Leu Gly Lys
385                 390                 395                 400

<210> SEQ ID NO 25
<211> LENGTH: 401
<212> TYPE: PRT
<213> ORGANISM: Artificial Sequence
<220> FEATURE:
<223> OTHER INFORMATION: amino acid sequence of modified IL-7(MMMM)
      fused hyFc

<400> SEQUENCE: 25

Met Met Met Met Asp Cys Asp Ile Glu Gly Lys Asp Gly Lys Gln Tyr
1               5                   10                  15

Glu Ser Val Leu Met Val Ser Ile Asp Gln Leu Leu Asp Ser Met Lys
                20                  25                  30

Glu Ile Gly Ser Asn Cys Leu Asn Asn Glu Phe Asn Phe Phe Lys Arg
            35                  40                  45

His Ile Cys Asp Ala Asn Lys Glu Gly Met Phe Leu Phe Arg Ala Ala
        50                  55                  60

Arg Lys Leu Arg Gln Phe Leu Lys Met Asn Ser Thr Gly Asp Phe Asp
65                  70                  75                  80

Leu His Leu Leu Lys Val Ser Glu Gly Thr Thr Ile Leu Leu Asn Cys
                85                  90                  95

Thr Gly Gln Val Lys Gly Arg Lys Pro Ala Ala Leu Gly Glu Ala Gln
            100                 105                 110

Pro Thr Lys Ser Leu Glu Glu Asn Lys Ser Leu Lys Glu Gln Lys Lys
        115                 120                 125

Leu Asn Asp Leu Cys Phe Leu Lys Arg Leu Leu Gln Glu Ile Lys Thr
    130                 135                 140

Cys Trp Asn Lys Ile Leu Met Gly Thr Lys Glu His Arg Asn Thr Gly
145                 150                 155                 160

Arg Gly Gly Glu Glu Lys Lys Lys Glu Lys Glu Lys Glu Glu Gln Glu
                165                 170                 175

Glu Arg Glu Thr Lys Thr Pro Glu Cys Pro Ser His Thr Gln Pro Leu
            180                 185                 190

Gly Val Phe Leu Phe Pro Pro Lys Pro Lys Asp Thr Leu Met Ile Ser
        195                 200                 205
```

```
Arg Thr Pro Glu Val Thr Cys Val Val Val Asp Val Ser Gln Glu Asp
    210             215                 220
Pro Glu Val Gln Phe Asn Trp Tyr Val Asp Gly Val Glu Val His Asn
225             230                 235                 240
Ala Lys Thr Lys Pro Arg Glu Glu Gln Phe Asn Ser Thr Tyr Arg Val
            245                 250                 255
Val Ser Val Leu Thr Val Leu His Gln Asp Trp Leu Asn Gly Lys Glu
                260                 265                 270
Tyr Lys Cys Lys Val Ser Asn Lys Gly Leu Pro Ser Ser Ile Glu Lys
            275                 280                 285
Thr Ile Ser Lys Ala Lys Gly Gln Pro Arg Glu Pro Gln Val Tyr Thr
    290                 295                 300
Leu Pro Pro Ser Gln Glu Glu Met Thr Lys Asn Gln Val Ser Leu Thr
305             310                 315                 320
Cys Leu Val Lys Gly Phe Tyr Pro Ser Asp Ile Ala Val Glu Trp Glu
            325                 330                 335
Ser Asn Gly Gln Pro Glu Asn Asn Tyr Lys Thr Thr Pro Pro Val Leu
                340                 345                 350
Asp Ser Asp Gly Ser Phe Phe Leu Tyr Ser Arg Leu Thr Val Asp Lys
            355                 360                 365
Ser Arg Trp Gln Glu Gly Asn Val Phe Ser Cys Ser Val Met His Glu
    370                 375                 380
Ala Leu His Asn His Tyr Thr Gln Lys Ser Leu Ser Leu Ser Leu Gly
385             390                 395                 400
Lys

<210> SEQ ID NO 26
<211> LENGTH: 397
<212> TYPE: PRT
<213> ORGANISM: Artificial Sequence
<220> FEATURE:
<223> OTHER INFORMATION: amino acid sequence of human IL-7 fused hyFc

<400> SEQUENCE: 26

Asp Cys Asp Ile Glu Gly Lys Asp Gly Lys Gln Tyr Glu Ser Val Leu
1               5                   10                  15
Met Val Ser Ile Asp Gln Leu Leu Asp Ser Met Lys Glu Ile Gly Ser
                20                  25                  30
Asn Cys Leu Asn Asn Glu Phe Asn Phe Phe Lys Arg His Ile Cys Asp
            35                  40                  45
Ala Asn Lys Glu Gly Met Phe Leu Phe Arg Ala Ala Arg Lys Leu Arg
    50                  55                  60
Gln Phe Leu Lys Met Asn Ser Thr Gly Asp Phe Asp Leu His Leu Leu
65              70                  75                  80
Lys Val Ser Glu Gly Thr Thr Ile Leu Leu Asn Cys Thr Gly Gln Val
                85                  90                  95
Lys Gly Arg Lys Pro Ala Ala Leu Gly Glu Ala Gln Pro Thr Lys Ser
            100                 105                 110
Leu Glu Glu Asn Lys Ser Leu Lys Glu Gln Lys Lys Leu Asn Asp Leu
        115                 120                 125
Cys Phe Leu Lys Arg Leu Leu Gln Glu Ile Lys Thr Cys Trp Asn Lys
    130                 135                 140
Ile Leu Met Gly Thr Lys Glu His Arg Asn Thr Gly Arg Gly Gly Glu
145             150                 155                 160
Glu Lys Lys Lys Glu Lys Glu Lys Glu Glu Gln Glu Glu Arg Glu Thr
```

```
                    165                 170                 175
Lys Thr Pro Glu Cys Pro Ser His Thr Gln Pro Leu Gly Val Phe Leu
                180                 185                 190

Phe Pro Pro Lys Pro Lys Asp Thr Leu Met Ile Ser Arg Thr Pro Glu
            195                 200                 205

Val Thr Cys Val Val Val Asp Val Ser Gln Glu Asp Pro Glu Val Gln
        210                 215                 220

Phe Asn Trp Tyr Val Asp Gly Val Glu Val His Asn Ala Lys Thr Lys
225                 230                 235                 240

Pro Arg Glu Glu Gln Phe Asn Ser Thr Tyr Arg Val Val Ser Val Leu
                245                 250                 255

Thr Val Leu His Gln Asp Trp Leu Asn Gly Lys Glu Tyr Lys Cys Lys
            260                 265                 270

Val Ser Asn Lys Gly Leu Pro Ser Ser Ile Glu Lys Thr Ile Ser Lys
        275                 280                 285

Ala Lys Gly Gln Pro Arg Glu Pro Gln Val Tyr Thr Leu Pro Pro Ser
    290                 295                 300

Gln Glu Glu Met Thr Lys Asn Gln Val Ser Leu Thr Cys Leu Val Lys
305                 310                 315                 320

Gly Phe Tyr Pro Ser Asp Ile Ala Val Glu Trp Glu Ser Asn Gly Gln
                325                 330                 335

Pro Glu Asn Asn Tyr Lys Thr Thr Pro Pro Val Leu Asp Ser Asp Gly
            340                 345                 350

Ser Phe Phe Leu Tyr Ser Arg Leu Thr Val Asp Lys Ser Arg Trp Gln
        355                 360                 365

Glu Gly Asn Val Phe Ser Cys Ser Val Met His Glu Ala Leu His Asn
    370                 375                 380

His Tyr Thr Gln Lys Ser Leu Ser Leu Gly Lys
385                 390                 395

<210> SEQ ID NO 27
<211> LENGTH: 395
<212> TYPE: PRT
<213> ORGANISM: Artificial Sequence
<220> FEATURE:
<223> OTHER INFORMATION: amino acid sequence of human IL-7 fused
      nonlytic mouse Fc

<400> SEQUENCE: 27

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
                20                  25                  30

Asn Cys Leu Asn Asn Glu Phe Asn Phe Phe Lys Arg His Ile Cys Asp
            35                  40                  45

Ala Asn Lys Glu Gly Met Phe Leu Phe Arg Ala Ala Arg Lys Leu Arg
        50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125
```

```
Cys Phe Leu Lys Arg Leu Leu Gln Glu Ile Lys Thr Cys Trp Asn Lys
        130                 135                 140

Ile Leu Met Gly Thr Lys Glu His Ala Ser Ala Glu Pro Arg Gly Pro
145                 150                 155                 160

Thr Ile Lys Pro Cys Pro Pro Cys Lys Cys Pro Ala Pro Asn Leu Glu
                165                 170                 175

Gly Gly Pro Ser Val Phe Ile Phe Pro Pro Lys Ile Lys Asp Val Leu
            180                 185                 190

Met Ile Ser Leu Ser Pro Ile Val Thr Cys Val Val Asp Val Ser
        195                 200                 205

Glu Asp Asp Pro Asp Val Gln Ile Ser Trp Phe Val Asn Asn Val Glu
210                 215                 220

Val His Thr Ala Gln Thr Gln Thr His Arg Glu Asp Tyr Asn Ser Thr
225                 230                 235                 240

Leu Arg Val Val Ser Ala Leu Pro Ile Gln His Gln Asp Trp Met Ser
                245                 250                 255

Gly Lys Ala Phe Ala Cys Ala Val Asn Asn Lys Asp Leu Pro Ala Pro
            260                 265                 270

Ile Glu Arg Thr Ile Ser Lys Pro Lys Gly Ser Val Arg Ala Pro Gln
        275                 280                 285

Val Tyr Val Leu Pro Pro Glu Glu Glu Met Thr Lys Lys Gln Val
290                 295                 300

Thr Leu Thr Cys Met Val Thr Asp Phe Met Pro Glu Asp Ile Tyr Val
305                 310                 315                 320

Glu Trp Thr Asn Asn Gly Lys Thr Glu Leu Asn Tyr Lys Asn Thr Glu
                325                 330                 335

Pro Val Leu Asp Ser Asp Gly Ser Tyr Phe Met Tyr Ser Lys Leu Arg
            340                 345                 350

Val Glu Lys Lys Asn Trp Val Glu Arg Asn Ser Tyr Ser Cys Ser Val
        355                 360                 365

Val His Glu Gly Leu His Asn His His Thr Thr Lys Ser Phe Ser Arg
370                 375                 380

Thr Pro Gly Lys Gly Gly Gly Asn Ser Gly Ser
385                 390                 395

<210> SEQ ID NO 28
<211> LENGTH: 531
<212> TYPE: DNA
<213> ORGANISM: Artificial Sequence
<220> FEATURE:
<223> OTHER INFORMATION: nucleotide sequence of human IL-7

<400> SEQUENCE: 28
atgttccacg tgagcttcag gtacatcttc ggcctgccac ccctgatcct ggtgctgctg      60
cctgtggcca gctccgactg cgacatcgag ggaaaagacg gcaagcagta cgaaagcgtg     120
ctgatggtgt ccatcgacca gctgctggat tctatgaagg agattgggag taactgcctg     180
aacaatgagt tcaacttctt caaacggcac atttgtgatg ccaacaagga gggaatgttc     240
ctgtttcggg ccgctagaaa actgaggcag ttcctgaaga tgaacagcac cggagacttt     300
gatctgcatc tgctgaaagt gtctgagggc accacaatcc tgctgaactg cactgggcag     360
gtgaaaggaa ggaagcctgc cgctctggga gaggctcagc caaccaagtc actggaggaa     420
aacaaaagcc tgaaggaaca gaagaaactg aatgacctgt gctttctgaa acggctgctg     480
caggagatca aacatgttg gaacaagatt ctgatgggca caaggaaca c               531
```

<210> SEQ ID NO 29
<211> LENGTH: 534
<212> TYPE: DNA
<213> ORGANISM: Artificial Sequence
<220> FEATURE:
<223> OTHER INFORMATION: nucleotide sequence of modified IL-7(M)

<400> SEQUENCE: 29

```
atgttccacg tgagcttcag atacatcttc ggcctgcccc ccctgatcct ggtgctgctg      60
cccgtggcca gcagcatgga ctgcgacatc gagggcaagg acggcaagca gtacgagagc     120
gtgctgatgg tgagcatcga ccagctgctg gacagcatga aggagatcgg cagcaactgc     180
ctgaacaacg agttcaactt cttcaagaga cacatctgcg acgccaacaa ggagggcatg     240
ttcctgttca gagccgccag aaagctgaga cagttcctga gatgaacag caccggcgac     300
ttcgacctgc acctgctgaa ggtgagcgag ggcacaacca tcctgctgaa ctgcaccggc     360
caggtgaagg gcagaaagcc cgccgccctg gcgaggccc agcccaccaa gagcctggag     420
gagaacaaga gcctgaagga gcagaagaag ctgaacgacc tgtgcttcct gaagagactg     480
ctgcaggaga tcaagacctg ctggaacaag atcctgatgg gcaccaagga gcac           534
```

<210> SEQ ID NO 30
<211> LENGTH: 537
<212> TYPE: DNA
<213> ORGANISM: Artificial Sequence
<220> FEATURE:
<223> OTHER INFORMATION: nucleotide sequence of modified IL-7(MM)

<400> SEQUENCE: 30

```
atgttccacg tgagcttcag atacatcttc ggcctgcccc ccctgatcct ggtgctgctg      60
cccgtggcca gcagcatgat ggactgcgac atcgagggca aggacggcaa gcagtacgag     120
agcgtgctga tggtgagcat cgaccagctg ctggacagca tgaaggagat cggcagcaac     180
tgcctgaaca acgagttcaa cttcttcaag agacacatct gcgacgccaa caaggagggc     240
atgttcctgt tcagagccgc cagaaagctg agacagttcc tgaagatgaa cagcaccggc     300
gacttcgacc tgcacctgct gaaggtgagc gagggcacaa ccatcctgct gaactgcacc     360
ggccaggtga agggcagaaa gcccgccgcc ctgggcgagg cccagcccac caagagcctg     420
gaggagaaca gagcctgaa ggagcagaag aagctgaacg acctgtgctt cctgaagaga     480
ctgctgcagg agatcaagac ctgctggaac aagatcctga tgggcaccaa ggagcac       537
```

<210> SEQ ID NO 31
<211> LENGTH: 540
<212> TYPE: DNA
<213> ORGANISM: Artificial Sequence
<220> FEATURE:
<223> OTHER INFORMATION: nucleotide sequence of modified IL-7(MMM)

<400> SEQUENCE: 31

```
atgttccacg tgagcttcag atacatcttc ggcctgcccc ccctgatcct ggtgctgctg      60
cccgtggcca gcagcatgat gatggactgc gacatcgagg gcaaggacgg caagcagtac     120
gagagcgtgc tgatggtgag catcgaccag ctgctggaca gcatgaagga gatcggcagc     180
aactgcctga caacgagtt caacttcttc aagagacaca tctgcgacgc caacaaggag     240
ggcatgttcc tgttcagagc cgccagaaag ctgagacagt tcctgaagat gaacagcacc     300
ggcgacttcg acctgcacct gctgaaggtg agcgagggca caaccatcct gctgaactgc     360
accggccagg tgaagggcag aaagcccgcc gccctgggcg aggcccagcc caccaagagc     420
```
ctggaggaga acaagagcct gaaggagcag aagaagctga acgacctgtg cttcctgaag    480
agactgctgc aggagatcaa gacctgctgg aacaagatcc tgatgggcac caaggagcac    540

<210> SEQ ID NO 32
<211> LENGTH: 540
<212> TYPE: DNA
<213> ORGANISM: Artificial Sequence
<220> FEATURE:
<223> OTHER INFORMATION: nucleotide sequence of modified IL-7(MGM)

<400> SEQUENCE: 32
atgttccacg tgagcttcag gtacatcttc ggcctgccac ccctgatcct ggtgctgctg    60
cctgtggcca gctccatggg gatggactgc gacatcgagg gaaaagacgg caagcagtac    120
gaaagcgtgc tgatggtgtc catcgaccag ctgctggatt ctatgaagga gattgggagt    180
aactgcctga acaatgagtt caacttcttc aaacggcaca tttgtgatgc caacaaggag    240
ggaatgttcc tgtttcgggc cgctagaaaa ctgaggcagt tcctgaagat aacagcacc     300 ggagactttg atctgcatct gctgaaagtg tctgagggca ccacaatcct gctgaactgc    360
actgggcagg tgaaaggaag gaagcctgcc gctctgggag aggctcagcc aaccaagtca    420
ctggaggaaa acaaaagcct gaaggaacag aagaaactga atgacctgtg ctttctgaaa    480
cggctgctgc aggagatcaa acatgttgg aacaagattc tgatgggcac caaggagcac    540

<210> SEQ ID NO 33
<211> LENGTH: 540
<212> TYPE: DNA
<213> ORGANISM: Artificial Sequence
<220> FEATURE:
<223> OTHER INFORMATION: nucleotide sequence of modified IL-7(DDD)

<400> SEQUENCE: 33
atgttccacg tgagcttcag atacatcttc ggcctgcccc ccctgatcct ggtgctgctg    60
cccgtggcca gcagcgacga tgacgactgc gacatcgagg gcaaggacgg caagcagtac    120
gagagcgtgc tgatggtgag catcgaccag ctgctggaca gcatgaagga gatcggcagc    180
aactgcctga acaacgagtt caacttcttc aagagacaca tctgcgacgc caacaaggag    240
ggcatgttcc tgttcagagc cgccagaaag ctgagacagt tcctgaagat aacagcacc    300 ggcgacttcg acctgcacct gctgaaggtg agcgagggca caaccatcct gctgaactgc    360
accggccagg tgaagggcag aaagcccgcc gccctgggcg aggcccagcc caccaagagc    420
ctggaggaga acaagagcct gaaggagcag aagaagctga cgacctgtg cttcctgaag    480 agactgctgc aggagatcaa gacctgctgg aacaagatcc tgatgggcac caaggagcac    540

<210> SEQ ID NO 34
<211> LENGTH: 543
<212> TYPE: DNA
<213> ORGANISM: Artificial Sequence
<220> FEATURE:
<223> OTHER INFORMATION: nucleotide sequence of modified IL-7(MMMM)

<400> SEQUENCE: 34
atgttccacg tgagcttcag atacatcttc ggcctgcccc ccctgatcct ggtgctgctg    60
cccgtggcca gcagcatgat gatgatggac tgcgacatcg agggcaagga cggcaagcag    120
tacgagagcg tgctgatggt gagcatcgac cagctgctgg acagcatgaa ggagatcggc    180
agcaactgcc tgaacaacga gttcaacttc ttcaagagac acatctgcga cgccaacaag    240

```
gagggcatgt tcctgttcag agccgccaga aagctgagac agttcctgaa gatgaacagc      300
accggcgact cgacctgca cctgctgaag gtgagcgagg cacaaccat cctgctgaac        360 tgcaccggcc aggtgaaggg cagaaagccc gccgccctgg gcgaggccca gcccaccaag      420
agcctggagg agaacaagag cctgaaggag cagaagaagc tgaacgacct gtgcttcctg      480
aagagactgc tgcaggagat caagacctgc tggaacaaga tcctgatggg caccaaggag      540
cac                                                                    543
```

<210> SEQ ID NO 35
<211> LENGTH: 1284
<212> TYPE: DNA
<213> ORGANISM: Artificial Sequence
<220> FEATURE:
<223> OTHER INFORMATION: nucleotide sequence of modified IL-7(M) fused
      hyFc

<400> SEQUENCE: 35

```
atgttccacg tgagcttcag atacatcttc ggcctgcccc ccctgatcct ggtgctgctg      60
cccgtggcca gcagcatgga ctgcgacatc gagggcaagg acggcaagca gtacgagagc    120
gtgctgatgg tgagcatcga ccagctgctg gacagcatga aggagatcgg cagcaactgc    180
ctgaacaacg agttcaactt cttcaagaga cacatctgcg acgccaacaa ggagggcatg    240
ttcctgttca gagccgccag aaagctgaga cagttcctga agatgaacag caccggcgac    300
ttcgacctgc acctgctgaa ggtgagcgag ggcacaacca tcctgctgaa ctgcaccggc    360
caggtgaagg gcagaaagcc cgccgccctg ggcgaggccc agcccaccaa gagcctggag    420
gagaacaaga gcctgaagga gcagaagaag ctgaacgacc tgtgcttcct gaagagactg    480
ctgcaggaga tcaagacctg ctggaacaag atcctgatgg gcaccaagga gcacaggaac    540
acaggcagag gcggcgagga agaagaagag gaaggagag aggaggagca ggaggaaaga    600
gagaccaaga cccccgagtg ccccagccac acccagcccc tgggcgtgtt cctgttccct    660
cccaagccca aggacaccct gatgatcagc agaacccccg aggtgacctg cgtggtcgtg    720
gatgtgagcc aggaagatcc gaagtgcag ttcaactggt acgtggatgg cgtggaagtg    780
cacaacgcca agaccaagcc cagagaagag cagttcaact ccacctacag agtggtgagc    840
gtgctgaccg tgctgcacca ggactggctg aacggcaagg agtacaagtg caaggtgtcc    900
aacaaaggcc tgcccagctc catcgagaag accatcagca agccaaagg ccagcccaga    960 gaaccccagg tgtacaccct gcctcccagc aggaagaga tgaccaagaa ccaggtgtcc   1020
ctgacctgcc tggtgaaagg cttctacccc agcgacatcg ccgtggagtg ggaaagcaac   1080
ggccagcccg agaacaatta caagacaacc ctcccgtgc tggatagcga tggcagcttc   1140
tttctgtaca gcagactgac cgtggacaag agcagatggc aggaaggcaa cgtgttcagc   1200
tgcagcgtga tgcacgaagc cctgcacaac cactacaccc agaagagcct gtccctgagc   1260
ctgggcaagt gactcgagtc taga                                         1284
```

<210> SEQ ID NO 36
<211> LENGTH: 1272
<212> TYPE: DNA
<213> ORGANISM: Artificial Sequence
<220> FEATURE:
<223> OTHER INFORMATION: nucleotide sequence of modified IL-7(MM) fused
      hyFc

<400> SEQUENCE: 36

```
atgttccacg tgagcttcag atacatcttc ggcctgcccc ccctgatcct ggtgctgctg      60
```

```
cccgtggcca gcagcatgat ggactgcgac atcgagggca aggacggcaa gcagtacgag      120
agcgtgctga tggtgagcat cgaccagctg ctggacagca tgaaggagat cggcagcaac      180
tgcctgaaca acgagttcaa cttcttcaag agacacatct gcgacgccaa caaggagggc      240
atgttcctgt tcagagccgc cagaaagctg agacagttcc tgaagatgaa cagcaccggc      300
gacttcgacc tgcacctgct gaaggtgagc gagggcacaa ccatcctgct gaactgcacc      360
ggccaggtga agggcagaaa gcccgccgcc ctgggcgagg cccagcccac caagagcctg      420
gaggagaaca gagcctgaa ggagcagaag aagctgaacg acctgtgctt cctgaagaga       480
ctgctgcagg agatcaagac ctgctggaac aagatcctga tgggcaccaa ggagcacagg      540
aacacaggca gaggcggcga ggagaagaag aaggagaagg agaaggagga gcaggaggaa      600
agagagacca gaccccccga gtgccccagc cacacccagc ccctgggcgt gttcctgttc      660
cctcccaagc ccaaggacac cctgatgatc agcagaaccc ccgaggtgac ctgcgtggtc      720
gtggatgtga gccaggaaga tcccgaagtg cagttcaact ggtacgtgga tggcgtggaa      780
gtgcacaacg ccaagaccaa gcccagagaa gagcagttca ctccaccta cagagtggtg       840 agcgtgctga ccgtgctgca ccaggactgg ctgaacggca aggagtacaa gtgcaaggtg      900
tccaacaaag gcctgcccag ctccatcgag aagaccatca gcaaagccaa aggccagccc      960
agagaacccc aggtgtacac cctgcctccc agccaggaag agatgaccaa gaaccaggtg      1020
tccctgacct gcctggtgaa aggcttctac cccagcgaca tcgccgtgga gtgggaaagc      1080
aacggccagc ccgagaacaa ttacaagaca acccctcccg tgctggatag cgatggcagc      1140
ttctttctgt acagcagact gaccgtggac aagagcagat ggcaggaagg caacgtgttc      1200
agctgcagcg tgatgcacga agccctgcac aaccactaca cccagaagag cctgtccctg      1260
agcctgggca ag                                                          1272
```

<210> SEQ ID NO 37
<211> LENGTH: 1275
<212> TYPE: DNA
<213> ORGANISM: Artificial Sequence
<220> FEATURE:
<223> OTHER INFORMATION: nucleotide sequence of modified IL-7(MMM) fused hyFc

<400> SEQUENCE: 37

```
atgttccacg tgagcttcag atacatcttc ggcctgcccc ccctgatcct ggtgctgctg       60
cccgtggcca gcagcatgat gatggactgc gacatcgagg gcaaggacgg caagcagtac      120
gagagcgtgc tgatggtgag catcgaccag ctgctggaca gcatgaagga gatcggcagc      180
aactgcctga caacgagtt caacttcttc aagagacaca tctgcgacgc caacaaggag       240
ggcatgttcc tgttcagagc cgccagaaag ctgagacagt tcctgaagat gaacagcacc      300
ggcgacttcg acctgcacct gctgaaggtg agcgagggca aaccatcct gctgaactgc       360 accggccagg tgaagggcag aaagcccgcc gccctgggcg aggcccagcc caccaagagc      420
ctggaggaga acaagagcct gaaggagcag aagaagctga cgacctgtg cttcctgaag       480 agactgctgc aggagatcaa gacctgctgg aacaagatcc tgatgggcac caaggagcac      540
aggaacacag gcagaggcgg cgaggagaag aaggagaagg agaaggagga ggagcaggag      600
gaaagagaga ccaagacccc cgagtgcccc agccacaccc agcccctggg cgtgttcctg      660
ttccctccca gcccaagga cacctgatg atcagcagaa cccccgaggt gacctgcgtg       720
gtcgtggatg tgagccagga agatcccgaa gtgcagttca actggtacgt ggatggcgtg      780
```

```
gaagtgcaca acgccaagac caagcccaga gaagagcagt tcaactccac ctacagagtg    840
gtgagcgtgc tgaccgtgct gcaccaggac tggctgaacg gcaaggagta caagtgcaag    900
gtgtccaaca aaggcctgcc cagctccatc gagaagacca tcagcaaagc caaaggccag    960
cccagagaac cccaggtgta caccctgcct cccagccagg aagagatgac caagaaccag   1020
gtgtccctga cctgcctggt gaaaggcttc taccccagcg acatcgccgt ggagtgggaa   1080
agcaacggcc agcccgagaa caattacaag acaacccctc ccgtgctgga tagcgatggc   1140
agcttctttc tgtacagcag actgaccgtg gacaagagca gatggcagga aggcaacgtg   1200
ttcagctgca gcgtgatgca cgaagccctg cacaaccact acacccagaa gagcctgtcc   1260
ctgagcctgg gcaag                                                    1275
```

<210> SEQ ID NO 38
<211> LENGTH: 1275
<212> TYPE: DNA
<213> ORGANISM: Artificial Sequence
<220> FEATURE:
<223> OTHER INFORMATION: nucleotide sequence of modified IL-7(MGM) fused hyFc

<400> SEQUENCE: 38

```
atgttccacg tgagcttcag gtacatcttc ggcctgccac ccctgatcct ggtgctgctg     60
cctgtggcca gctccatggg gatggactgc gacatcgagg gaaagacgg caagcagtac    120 gaaagcgtgc tgatggtgtc catcgaccag ctgctggatt ctatgaagga gattgggagt    180
aactgcctga caatgagtt caacttcttc aaacggcaca tttgtgatgc caacaaggag    240
ggaatgttcc tgtttcgggc cgctagaaaa ctgaggcagt tcctgaagat gaacagcacc    300
ggagactttg atctgcatct gctgaaagtg tctgagggca ccacaatcct gctgaactgc    360
actgggcagg tgaaaggaag gaagcctgcc gctctgggag aggctcagcc aaccaagtca    420
ctggaggaaa acaaaagcct gaaggaacag aagaaactga atgacctgtg ctttctgaaa    480
cggctgctgc aggagatcaa acatgttgg aacaagattc tgatgggcac aaaggaacac    540
cgcaatactg gcggggcgg ggaggaaaag aaaaaggaga aggaaaagga ggaacaggag    600
gaaagagaga ctaagacccc agaatgtccc agccatactc agccctgggg ggtgttcctg    660 tttccccta aacctaagga taccctgatg atcagcagga cacccgaggt gacctgcgtg    720
gtcgtggatg tgagccagga agatcccgaa gtgcagttca actggtacgt ggatggcgtg    780
gaagtgcaca acgccaagac caagcccaga gaagagcagt tcaactccac ctacagagtg    840
gtgagcgtgc tgaccgtgct gcaccaggac tggctgaacg gcaaggagta caagtgcaag    900
gtgtccaaca aaggcctgcc cagctccatc gagaagacca tcagcaaagc caaaggccag    960
cccagagaac cccaggtgta caccctgcct cccagccagg aagagatgac caagaaccag   1020
gtgtccctga cctgcctggt gaaaggcttc taccccagcg acatcgccgt ggagtgggaa   1080
agcaacggcc agcccgagaa caattacaag acaacccctc ccgtgctgga tagcgatggc   1140
agcttctttc tgtacagcag actgaccgtg gacaagagca gatggcagga aggcaacgtg   1200
ttcagctgca gcgtgatgca cgaagccctg cacaaccact acacccagaa gagcctgtcc   1260
ctgagcctgg gcaag                                                    1275
```

<210> SEQ ID NO 39
<211> LENGTH: 1278
<212> TYPE: DNA
<213> ORGANISM: Artificial Sequence

```
<220> FEATURE:
<223> OTHER INFORMATION: nucleotide sequence of modified IL-7(MMMM)
      fused hyFc

<400> SEQUENCE: 39
atgttccacg tgagcttcag atacatcttc ggcctgcccc ccctgatcct ggtgctgctg       60
cccgtggcca gcagcatgat gatgatggac tgcgacatcg agggcaagga cggcaagcag      120
tacgagagcg tgctgatggt gagcatcgac cagctgctgg acagcatgaa ggagatcggc      180
agcaactgcc tgaacaacga gttcaacttc ttcaagagac acatctgcga cgccaacaag      240
gagggcatgt tcctgttcag agccgccaga aagctgagac agttcctgaa gatgaacagc      300
accggcgact tcgacctgca cctgctgaag gtgagcgagg gcacaaccat cctgctgaac      360
tgcaccggcc aggtgaaggg cagaaagccc gccgccctgg gcgaggccca gcccaccaag      420
agcctggagg agaacaagag cctgaaggag cagaagagc tgaacgacct gtgcttcctg       480
aagagactgc tgcaggagat caagacctgc tggaacaaga tcctgatggg caccaaggag      540
cacaggaaca caggcagagg cggcgaggag aagaagaagg agaaggagaa ggaggagcag      600
gaggaaagag agaccaagac ccccgagtgc ccagccaca cccagcccct gggcgtgttc        660
ctgttccctc ccaagcccaa ggacaccctg atgatcagca gaacccccga ggtgacctgc      720
gtggtcgtgg atgtgagcca ggaagatccc gaagtgcagt tcaactggta cgtggatggc      780
gtggaagtgc acaacgccaa gaccaagccc agagaagagc agttcaactc cacctacaga      840
gtggtgagcg tgctgaccgt gctgcaccag gactggctga acggcaagga gtacaagtgc      900
aaggtgtcca acaaaggcct gcccagctcc atcgagaaga ccatcagcaa agccaaaggc      960
cagcccagag aacccaggt gtacaccctg cctcccagcc aggaagagat gaccaagaac      1020
caggtgtccc tgacctgcct ggtgaaaggc ttctacccca gcgacatcgc cgtggagtgg     1080
gaaagcaacg gccagcccga gaacaattac aagacaaccc ctcccgtgct ggatagcgat     1140
ggcagcttct tctgtacag cagactgacc gtggacaaga gcagatggca ggaaggcaac      1200
gtgttcagct gcagcgtgat gcacgaagcc ctgcacaacc actacaccca gaagagcctg     1260
tccctgagcc tgggcaag                                                   1278

<210> SEQ ID NO 40
<211> LENGTH: 4
<212> TYPE: PRT
<213> ORGANISM: Artificial Sequence
<220> FEATURE:
<223> OTHER INFORMATION: oligopeptides conjugated with IL-7

<400> SEQUENCE: 40

Met Met Met Met
1

<210> SEQ ID NO 41
<211> LENGTH: 20
<212> TYPE: DNA
<213> ORGANISM: Artificial Sequence
<220> FEATURE:
<223> OTHER INFORMATION: Forward primer for detecting NS-1 gene

<400> SEQUENCE: 41
tgcgggaaag cagatagtgg                                                   20

<210> SEQ ID NO 42
<211> LENGTH: 20
<212> TYPE: DNA
```

```
<213> ORGANISM: Artificial Sequence
<220> FEATURE:
<223> OTHER INFORMATION: Reverse primer for detecting NS-1 gene

<400> SEQUENCE: 42
tcagttaggt agcgcgaagc                                               20

<210> SEQ ID NO 43
<211> LENGTH: 18
<212> TYPE: DNA
<213> ORGANISM: Artificial Sequence
<220> FEATURE:
<223> OTHER INFORMATION: Forward primer for detecting L32 gene

<400> SEQUENCE: 43
gaaactggcg gaaaccca                                                 18

<210> SEQ ID NO 44
<211> LENGTH: 20
<212> TYPE: DNA
<213> ORGANISM: Artificial Sequence
<220> FEATURE:
<223> OTHER INFORMATION: Reverse primer for detecting L32 gene

<400> SEQUENCE: 44
ggatctggcc cttgaacctt                                               20
```

What is claimed is:

1. A method of treating a disease caused by an influenza virus in a subject in need thereof, comprising administering to the subject an interleukin-7 (IL-7) fusion protein, which comprises a human IL-7 protein, an immunoglobulin Fc region, and an oligopeptide, wherein the immunoglobulin Fc region and/or the oligopeptide is linked to the human IL-7 protein, wherein the human IL-7 protein comprises amino acid residues 26-178 of the amino acid sequence set forth in SEQ ID NO: 1, wherein the immunoglobulin Fc region comprises the amino acid sequence set forth in any one of SEQ ID NOs: 9 to 14, and wherein the oligopeptide is selected from the group consisting of methionine, glycine, methionine-methionine, glycine-glycine, methionine-glycine, glycine-methionine, methionine-methionine-methionine, methionine-methionine-glycine, methionine-glycine-methionine, glycine-methionine-methionine, methionine-glycine-glycine, glycine-methionine-glycine, glycine-glycine-methionine, and glycine-glycine-glycine.

2. The method of claim 1, wherein the human IL-7 protein does not comprise amino acid residues 1-25 of the amino acid sequence set forth in SEQ ID NO: 1.

3. The method of claim 1, wherein the human IL-7 protein consists of amino acid residues 26-178 of the amino acid sequence set forth in SEQ ID NO: 1.

4. The method of claim 1, wherein the human IL-7 protein consists essentially of amino acid residues 26-178 of the amino acid sequence set forth in SEQ ID NO: 1.

5. The method of claim 1, wherein the IL-7 fusion protein is represented by the following formula:

N'-Fc-A-IL-7-C' or (Formula I)

or N'-A-IL-7-Fc-C' (Formula II)

wherein:
N' is the N-terminus of the IL-7 fusion protein;
C' is the C-terminus of the IL-7 fusion protein;
A is the oligopeptide;
Fc is the immunoglobulin Fc region; and
IL-7 is the human IL-7 protein.

6. The method of claim 1, wherein the IL-7 fusion protein comprises the amino acid sequence set forth in any one of SEQ ID NOs: 21, 22, 23, 24, 25, 26, and 27.

7. The method of claim 1, wherein the influenza virus is H7N9, H5N1, H5N2, H3N2, or H1N1.

8. The method of claim 1, wherein the IL-7 fusion protein is administered to the subject via a local administration, intramuscular administration, intraperitoneal administration, or subcutaneous administration.

9. The method of claim 8, wherein the local administration comprises an intranasal administration.

10. A method of enhancing an immune response in a subject infected with an influenza virus, comprising administering to the subject an interleukin-7 (IL-7) fusion protein, which comprises a human IL-7 protein, an immunoglobulin Fc region, and an oligopeptide, wherein the immunoglobulin Fc region and/or the oligopeptide is linked to the human IL-7 protein, wherein the human IL-7 protein comprises amino acid residues 26-178 of the amino acid sequence set forth in SEQ ID NO: 1, and wherein the immunoglobulin Fc region comprises the amino acid sequence set forth in any one of SEQ ID NOs: 9 to 14, and wherein the oligopeptide is selected from the group consisting of methionine, glycine, methionine-methionine, glycine-glycine, methionine-glycine, glycine-methionine, methionine-methionine-methionine, methionine-methionine-glycine, methionine-glycine-methionine, glycine-methionine-methionine, methionine-glycine-glycine, glycine-methionine-glycine, glycine-glycine-methionine, and glycine-glycine-glycine.

11. The method of claim 10, wherein, compared to a corresponding subject that did not receive the administration, (a) the number of immune cells is increased within the lungs of the subject, (b) the amount of airway inflammation is reduced in the subject, or (c) both (a) and (b) after the administration.

12. The method of claim 11, wherein the immune cells comprise influenza-specific T cells.

13. A method of reducing a risk of an influenza virus infection in a subject in need thereof, comprising administering to the subject an interleukin-7 (IL-7) fusion protein, which comprises a human IL-7 protein, an immunoglobulin Fc region, and an oligopeptide, wherein the immunoglobulin Fc region and/or the oligopeptide is linked to the human IL-7 protein, wherein the human IL-7 protein comprises amino acid residues 26-178 of the amino acid sequence set forth in SEQ ID NO: 1, wherein the immunoglobulin Fc region comprises the amino acid sequence set forth in any one of SEQ ID NOs: 9 to 14, and wherein the oligopeptide is selected from the group consisting of methionine, glycine, methionine-methionine, glycine-glycine, methionine-glycine, glycine-methionine, methionine-methionine-methionine, methionine-methionine-glycine, methionine-glycine-methionine, glycine-methionine-methionine, methionine-glycine-glycine, glycine-methionine-glycine, glycine-glycine-methionine, and glycine-glycine-glycine.

14. The method of claim 10, wherein the IL-7 fusion protein comprises the amino acid sequence set forth in any one of SEQ ID NOs: 21, 22, 23, 24, 25, 26, and 27.

15. The method of claim 13, wherein the IL-7 fusion protein comprises the amino acid sequence set forth in any one of SEQ ID NOs: 21, 22, 23, 24, 25, 26, and 27.

16. The method of claim 10, wherein the IL-7 fusion protein is administered to the subject via a local administration, intramuscular administration, intraperitoneal administration, or subcutaneous administration.

17. The method of claim 13, wherein the IL-7 fusion protein is administered to the subject via a local administration, intramuscular administration, intraperitoneal administration, or subcutaneous administration.

* * * * *